United States Patent
Fernandez Garcia et al.

(10) Patent No.: US 9,976,170 B2
(45) Date of Patent: May 22, 2018

(54) METHOD FOR EVALUATING BACTERIAL CELL WALL INTEGRITY

(75) Inventors: Jose Luis Fernandez Garcia, Madrid (ES); Jaime Gosalvez Berenguer, Madrid (ES); German Bou Arevalo, Madrid (ES); Maria Tamayo Novas, Madrid (ES); Rebeca Santiso Brandariz, Madrid (ES)

(73) Assignee: UNIVERSIDAD AUTONOMA DE MADRID, Madrid (ES)

( * ) Notice: Subject to any disclaimer, the term of this patent is extended or adjusted under 35 U.S.C. 154(b) by 0 days. days.

(21) Appl. No.: 14/234,875

(22) PCT Filed: Jul. 26, 2012

(86) PCT No.: PCT/ES2012/070575
§ 371 (c)(1),
(2), (4) Date: Jan. 24, 2014

(87) PCT Pub. No.: WO2013/014324
PCT Pub. Date: Jan. 31, 2013

(65) Prior Publication Data
US 2014/0206573 A1 Jul. 24, 2014

(30) Foreign Application Priority Data
Jul. 26, 2011 (ES) .................................. 201131276

(51) Int. Cl.
*C12Q 1/18* (2006.01)
*C12Q 1/68* (2018.01)
(52) U.S. Cl.
CPC ............... *C12Q 1/18* (2013.01); *C12Q 1/689* (2013.01)
(58) Field of Classification Search
None
See application file for complete search history.

(56) References Cited

U.S. PATENT DOCUMENTS 5,895,751 A * 4/1999 Hattori .................... C12Q 1/18
435/21
8,492,086 B2 * 7/2013 Berenguer ......... C12N 15/1003
435/6.1
(Continued)

FOREIGN PATENT DOCUMENTS

EP 0135023 A2 3/1985
EP 1710320 A1 11/2006
(Continued)

OTHER PUBLICATIONS

NPL document "Abcam guide", a pdf from Abcam at http://www.abcam.com/ps/pdf/protocols/fixation_permeabilization.pdf accessed Jun. 6, 2016, published online since Jul. 16, 2007 according to Google.*

(Continued)

*Primary Examiner* — Renee Claytor
*Assistant Examiner* — Trent R Clarke
(74) *Attorney, Agent, or Firm* — Lucas & Mercanti, LLP

(57) ABSTRACT

The present invention relates to a method for evaluating the integrity of the cell wall of the bacteria present in a culture in the presence of an antibiotic acting on the bacterial cell wall which, from a practical point of view, allows quickly determining if a bacterium is sensitive or resistant to an antibiotic acting on the bacterial cell wall. Likewise, the present invention also relates to a lysis solution applicable in the preceding method, specifically affecting bacteria having the cell wall damaged by the action of an antibiotic acting on the bacterial cell wall, which allows distinguishing bacteria sensitive to said antibiotic from those resistant to said antibiotic.

5 Claims, 10 Drawing Sheets

(56) References Cited

U.S. PATENT DOCUMENTS

| | | | |
|---|---|---|---|
| 2009/0142798 | A1 | 6/2009 | Lee et al. |
| 2010/0129803 | A1* | 5/2010 | Gosalvez Berenguer ................ C12N 15/1003 435/6.16 |
| 2011/0151455 | A1 | 6/2011 | Stroot et al. |

FOREIGN PATENT DOCUMENTS

| | | | |
|---|---|---|---|
| EP | 2080811 | A1 | 7/2009 |
| EP | 2333105 | | 6/2011 |
| GB | 2128737 | | 5/1984 |
| WO | 9219763 | A1 | 11/1992 |
| WO | 02055015 | | 7/2002 |
| WO | 03048380 | | 6/2003 |
| WO | 2008089280 | | 7/2008 |

OTHER PUBLICATIONS

Zhe Zhang, Huihui Chen, Chunyan Xing, Mingyi Guo, Fugang Xu, Xiaodan Wang, Hermann J. Gruber, Bailin Zhang, and Jilin Tang, Sodium Citrate: A Universal Reducing Agent for Reduction / Decoration of Graphene Oxide with Au Nanoparticles, Nano Res. 2011, 4(6): 599-611.*

E. Keowmaneechai and D. J. McClements, Influence of EDTA and Citrate on Physicochemical Properties of Whey Protein-Stabilized Oil-in-Water Emulsions Containing CaCl2, 2002, J. Agric. Food Chem, vol. 50, pp. 7145-7153.*

Bergfeld et al., Safety Assessment of Tromethamine, Aminomethyl Propanediol, and Aminoethyl Propanediol as Used in Cosmetics, 2013, Cosmetic Ingredient Review, pp. i-18, accessed at http://www.cir-safety.org/sites/default/files/Tromet_092013_Rep.pdf on Jun. 7, 2016.*

José Luis Fernández, Lourdes Muriel, Vicente Goyanes, Enrique Segrelles, Jaime Gosálvez, Maria Enciso, Marie LaFromboise, and Christopher De Jonge, Simple determination of human sperm DNA fragmentation with an improved sperm chromatin dispersion test, 2005, Fertility and Sterility, vol. 84, No. 4, pp. 833-842.*

Jose Luis Fernandez, Lourdes Muriel, Maria Teresa Rivero, Vicente Goyanes, Rosana Vazquez and Juan G. Alvarez, The Sperm Chromatin Dispersion Test: A Simple Method for the Determination of Sperm DNA Fragmentation, 2003, Journal of Andrology, vol. 24, No. 1, pp. 59-66.*

Fernandez, J.L., et al., DNA Fragmentation in Microorganisms . . . , Applied and Environmental Microbiology, 2008, vol. 74, No. 19, pp. 5925-5933.

Singh, N.P., A Simple Method for Accurate Estimation . . . , Experimental Cell Research, 2000, vol. 256, No. 1, pp. 328-337.

Santiso, R., et al., A Rapid in Situ Procedure for Determination . . . , BMC Microbiology, 2011, vol. 11, pp. 191.

International Search Report issued in counterpart PCT Application No. PCT/ES2012/070575.

Bauer et al., "Antibiotic Susceptibility Testing by a Standardized Single Disk Method", The American Journal of Clinical Pathology, 1966, vol. 45, No. 4, pp. 493-496.

Nakao et al., "Light and Electron Microscopy of the Morphological Response of Escherichia coli and Serratia Marcescens to Cefmenoxime (SCE-1365), A New Broad-Spectrum Cephalosporin", The Journal of Antibiotics, 1981, vol. XXXIV, No. 8, pp. 1046-1054.

Kohanski et al., "A Common Mechanism of Cellular Death Induced by Bactericidal Antibiotics", Cell, 2007, vol. 130, pp. 797-810.

Hoettges et al., "Rapid determination of antibiotic resistance in E. coli using dielectrophoresis", Phys.Med.Biol., 2007, vol. 52, pp. 6001-6009.

Tamayo et al., "Rapid assessment of the effect of ciprofloxacin on chromosomal DNA from Escherichia coli using an in situ DNA fragmentation assay", BMC Microbiology, 2009, vol. 9, No. 69, pp. 1-11.

Roostalu et al., "Cell division in Escherichia coli cultures monitored at single cell resolution" BMC Microbiology, 2008, vol. 8, No. 68, pp. 1-14.

Lewis, "Persister cells, dormancy and infectious disease", Nature Reviews, 2007, vol. 5, pp. 48-56.

Nathan et al., "Identification of two new cell division genes that affect a high-molecular-weight penicillin-binding protein in Caulobacter crescentus", Journal of Bacteriology, 1988, vol. 170, No. 5, pp. 2319-2327.

Limbert et al., "Cefodizime, An Aminothiazolylcephalosporin I. In Vitro Activity", The Journal of Antibiotics, 1984, vol. XXXVII, No. 8, pp. 892-900.

Chantratita et al., "Antimicrobial resistance to ceftazidime involving loss of penicillin-binding protein 3 in Burkholderia pseudomallei", PNAS, 2011, vol. 108, No. 41, pp. 17165-17170.

Ingham et al., Rapid antibiotic sensitivity testing and trimethoprim-mediated filamentation of clinical isolates of the Enterobacteriaceae assayed on a novel porous culture support, Journal of Medical Microbiology, 2006, vol. 55, pp. 1511-1519.

Braga et al., "Cefodizime: effects of sub-inhibitory concentrations on adhesiveness and bacterial morphology of Staphylococcus aureus and Escherichia coli: comparison with cefotaxime and ceftriaxone", JAC, 1997, vol. 39, pp. 79-84.

Hashimoto et al., "Rapid Bacterial Testing Method by Size Distribution Measurement with Laser Light Scattering", The Transactions of the IECE of Japan, 1985, vol. E 68, No. 5, pp. 304-308.

Wiegand et al., "Effect of inoculum density on susceptibility of Plesiomonas shigelloides to cephalosporins", JAC, 2004, vol. 54, No. 2, pp. 418-423.

Hashimoto et al., "Measurement of Bacterial Size Distribution Using Laser Light Scattering", Japanese Journal of Medical Electronics and Biological Engineering, 1984, vol. 22, , Abstract.

Sass et al., "Antibiotic aclydepsipeptides activate ClpP peptidase to degrade the cell division protein Ftsz", PNAS, 2011, vol. 108, No. 42, pp. 17474-17479.

Curtis et al., "Competition of B-Lactam Antibiotics for the Penicillin-Binding Proteins of Pseudomonas aeruginosa, Enterobacter cloacae, Klebsiella aerogenes, Proteus rettgeri, and Escherichia coli:Comparison with Antibacterial Activity and Effects upon Bacterial Morphology", Antimicrobial Agents and Chemotherapy, 1979, vol. 16, No. 3, pp. 325-328.

Extended European Search Report for European Application No. EP12817952 dated Mar. 11, 2015. (8 Pages).

Response to Extended European Search Report and Amended Claims for European Application No. 12817952.0. (dated Oct. 5, 2015)(12 pages).

* cited by examiner

METHOD FOR EVALUATING BACTERIAL CELL WALL INTEGRITY

CROSS REFERENCE TO RELATED APPLICATION

This Application is a 371 of PCT/ES2012/070575 filed on Jul. 26, 2012, which claims the priority of Spanish Patent Application No. P201131276 filed on Jul. 26, 2011, both applications are incorporated herein by reference in their entirety.

TECHNICAL FIELD OF THE INVENTION

The present invention is encompassed within the field of biotechnology industry, and primarily that related to microbiology, the scope of application of which is in the health sector (human health, animal health, environmental health and basic health). The present invention relates to a method for evaluating the integrity of the cell wall of the bacteria present in a culture in the presence of an antibiotic acting on the bacterial cell wall which, from a practical point of view, allows quickly determining if a bacterium is sensitive or resistant to an antibiotic acting on the cell wall.

BACKGROUND OF THE INVENTION

The study on microorganism sensitivity to antimicrobial agents is one of the most important functions of clinical microbiology laboratories. The study is conducted by means of sensitivity testings or antibiogram, the main objective of which is to evaluate in the laboratory the response of a microorganism to one or several antimicrobial agents.

Some of the most commonly used methods in daily clinical practice include (i) diffusion methods such as disc-dish antibiogram based on the work of Bauer, Kirby et al. (Bauer A W, et al. Am. J. Clin. Pathol. 1966, 45:493-496) or the Epsilon-test or E-test method (AB Biodisk, Sweden), or (ii) dilution methods such as agar dilution method or broth microdilution method. By comparing diffusion methods to dilution methods, the latter are more technically complex and almost always more expensive, particularly when commercial microdilution panels are used. Microdilution methods in liquid medium are the most commonly used methods in routine clinical microbiology laboratory practice.

In many laboratories, the use of commercial panels is based on the use of semi-automatic incubation-reading-interpretation systems; this facilitates their use but has the drawback of an increased expenditure. Some companies have introduced on the market panels wherein the culture medium includes a fluorescent indicator that allows quickly obtaining (less than 8 hours) the results. In relation to the rapid determination of resistance to antibiotics acting on the bacterial wall, such as β-lactams, a fluorogenic compound that can be metabolized is added to the culture medium (patent application WO/1992/019763). If the organism grows with the antibiotic, the metabolism of the bacterium leads to the release of the fluorophore. If the organism does not grow, the fluorescence of the sample increases.

Another possibility is to use a color indicator compound, such as tetrazolium, which causes a color change after adding an electron carrier, such as phenazine methosulfate, in the event of sensitivity to the antibiotic. However, there are still not enough data to allow suggesting the regular use of such panels.

Several commercial companies are also evaluating expert systems (software) which facilitate the clinical interpretation of the obtained results; it is safe to assume that such systems will be widely used in the future. Several systems are available on the market today, MicroScan WalkAway, Vitek and Wider being the most outstanding ones. In the absence of greater clinical experience with the use of fluorescent indicators, the mean response time for obtaining the susceptibility of a specific microorganism to antimicrobial agents ranges, such as in the diffusion methods mentioned above, between 18 and 24 hours. Recently, the possibility of using a dielectrophoresis system that detects changes in the electrophysiology of the cell after administering the antibiotic has been pointed out (Hoettges K F, Dale J W, Hughes M P. *Rapid determination of antibiotic resistance in E. coli using dielectrophoresis. Phys Med Biol* 2007; 52:6001-6009).

Another development for antibiotics acting on the bacterial wall, such as β-lactams, consists of detecting by means of a specific substrate the activity of cytoplasmic enzymes that are released by the cell to the medium, if the antibiotic has been effective (European Patent EP0135023).

BACcelr8r™ is a platform under development by Accelr8 for automatically identifying microorganisms and studying their resistance to antibiotics. It does not use culture, the isolation of bacteria is not necessary either. It works by means of cassettes wherein each cassette corresponds to a sample. It uses an automated system with a microscope controlled by means of a computer, a digital camera and an analysis software. A pump maintains a flow of bacteria-containing medium in different conditions through the cassette. The antibiotic resistance analysis could be completed in 8 hours.

Patent application US2004/0014066 describes a method for detecting in a sample the activity of an antibiotic affecting cell integrity which comprises (a) providing a transformed microorganism comprising a nucleic acid encoding a promoter which is operably linked to a heterologous reporter gene capable of emitting a detectable signal, and (b) contacting the sample with the transformed microorganism, (c) observing said microorganism for said detectable signal, wherein the promoter is regulated by a two-component signal transduction system, wherein the components are (i) a receptor sensitive to changes in the cell envelope or membrane of the microorganism and (ii) a trans-acting factor which is activated in response to a stimulation by the receptor and which regulates the promoter.

Antibiotics Acting on the Bacterial Wall

The skeleton of bacterial cell wall is made up of a heteropolymer, the murein peptidoglycan. This macromolecule is formed by an alternating sequence of N-acetylglucosamine (NAG) and N-acetylmuramic acid (NAM) bound to one another by means of β-1,4 bonds. The chain is a straight, unbranched chain forming the basic structure of the cell wall. The N-acetylmuramic acid has a lactic acid group linking with a short peptide chain (tetrapeptide). The amino acids typical of this chain include L-alanine, D-glutamic acid, m-diaminopimelic acid or L-lysine or D-alanine.

The antibiotics which inhibit bacterial wall synthesis are different families of drugs acting on the different steps of bacterial wall synthesis:

cycloserine is a D-alanine analog and competitively inhibits the binding of this amino acid to the enzymes D-alanine-D-alanine synthetase and alanine racemase, preventing them from binding to the precursors of peptidoglycan.

fosfomycin blocks the synthesis of the precursors of peptidoglycan.

bacitracin inhibits the recycling of undecaprenyl, the lipid carrier which carries peptidoglycan to the outside of the cell.

the glucopeptide or glycopeptide antibiotics are a class of peptides with sugars bound thereto, such as in the bacterial cell wall, having a high affinity for the precursors of this structure. The most well known glycopeptide antibiotics are vancomycin and teicoplanin. Vancomycin performs its bactericidal action by inhibiting bacterial cell wall synthesis, binding to the D-alanine-D-alanine (D-Ala-D-Ala) fragment of the pentapeptide on the wall of Gram+ bacteria, blocking the incorporation of peptides on the cell wall. Secondarily, vancomycin would act through other mechanisms such as disrupting cytoplasmic membrane permeability and inhibiting RNA synthesis, which is performed after the drug has bound to the peptidoglycan.

the β-lactam antibiotics perform bactericidal function by interfering the transverse binding or interpeptide bridge necessary for cross-linking. They inhibit the activity of PBPs, serine proteases or transpeptidases, by binding to them in an irreversible manner.

other antibiotics interfering with wall synthesis are isoniazid, ethionamide and ethambutol. Like the cycloserine mentioned above, they are used in the treatment of mycobacterial infections. Isoniazid has bactericidal activity in the active replication phase. It affects mycolic acid synthesis, interrupting the elongation of fatty acids. Ethionamide also inhibits mycolic acid synthesis. Ethambutol interferes with cell wall arabinogalactan synthesis. The resistance to these antibiotics is due to the lack of penetration into the bacterium and/or modification of their cellular targets.

Antibiotic resistance causes tens of thousands of deaths every year. Many of these deaths could be avoided with an antibiotic treatment properly selected for effectiveness. Given the levels of resistance, it is necessary to prepare the bacterial culture, followed by an antibiogram. To complete the foregoing, the bacteria must usually grow for 2-3 days. The antibiogram itself usually requires at least one day of incubation, for common fast-growing bacteria.

For patients in critical condition in ICU, a rapid antibiotic treatment is important. Given the delay of the antibiogram, it is performed empirically. Such treatment is ineffective in 20-40% of the cases, and the change of treatment after the results of the antibiogram may no longer be effective. In this situation, it is important to have a rapid antibiogram system. The antibiotics acting on the bacterial wall, specifically β-lactams, are a very large group and the most commonly used in anti-infective therapy. It is of great interest to have rapid antibiogram systems for such antibiotics.

DESCRIPTION OF THE INVENTION

The authors of the present invention have discovered that one consequence of the activity which the antibiotics acting on the bacterial cell wall have on bacteria is the release of extracellular DNA fragments into the culture medium. To observe this effect, the inventors incubated a strain of *E. coli* sensitive to ampicillin (a β-lactam antibiotic) in the presence of said antibiotic, after which the culture was included in different microgels on several slides, to which proteinase K or DNAase I was administered (Examples 7 and 8). The cultures that were not treated with ampicillin did not show microgranular-fibrillar background in the preparation (FIG. 10a), whereas in the cultures treated with ampicillin a microgranular background was observed. When the cultures treated with ampicillin were incubated with proteinase K, the background remained unchanged (FIG. 10f), whereas when they were incubated with DNAase I, the background was no longer observed (FIG. 10 d), indicating that the observed background mainly includes extracellular DNA fragments originating from cells affected by the antibiotic. Said background was not observed when other types of antibiotics, such as the quinolonas, which do not act on the cell wall, were used.

Nevertheless, the inventors also observed that, when the bacterial culture is a mixed or contaminated culture, i.e., there is a mixture of sensitive or resistant cells, said method would not be very suitable as a strict discrimination criterion because despite the release of extracellular DNA fragments, the morphology of the bacteria is not changed by the action of the antibiotic, i.e., both the bacteria sensitive and resistant to the antibiotic show an apparently intact cell wall. To solve this problem, the inventors have designed a lysis solution that only affects the bacteria the cell wall of which has been previously damaged by the action of an antibiotic acting on the cell wall, and that when added to the bacterial culture which has been previously exposed to the action of said antibiotic, causes the release of bacterial nucleoid, a bacterium with a damaged cell wall then being observed (Examples 1 to 5). Therefore, the presence of bacterial nucleoid after applying the lysis solution is indicative of the presence of bacteria sensitive to the antibiotic.

Therefore, in one aspect the invention relates to a method for evaluating the integrity of the cell wall of a bacterium in a pure culture in the presence of an antibiotic acting on the bacterial cell wall which comprises:

i) adding to said pure culture of said bacterium an antibiotic acting on the bacterial cell wall, and ii) determining the presence of extracellular DNA fragments in the culture medium, wherein the presence of extracellular DNA fragments in the culture medium is indicative that the integrity of the cell wall of the bacterium has been damaged.

In another aspect, the invention relates to a method for evaluating the integrity of the cell wall of the bacteria present in a culture in the presence of an antibiotic acting on the bacterial cell wall which comprises:

i) adding to said culture an antibiotic acting on the bacterial cell wall, ii) adding lysis solution to the culture resulting from step i), wherein said lysis solution is a lysis solution specific for those bacteria the cell wall of which has been damaged by the antibiotic acting on the bacterial cell wall, and comprises a buffer with a pH comprised between 3 and 11.5, and iii) determining the presence of bacterial nucleoid, wherein the presence of bacterial nucleoid in the medium is indicative that the integrity of the cell wall of the bacteria has been damaged.

In another aspect, the invention relates to a method for determining the sensitivity of a bacterium to an antibiotic acting on the bacterial cell wall, which comprises measuring the integrity of the cell wall of said bacterium by means of a method according to the present invention, wherein if the integrity of the cell wall of the bacterium has been damaged, then the bacterium is sensitive to the antibiotic.

In another aspect, the invention relates to a method for designing an antibiotic therapy customized for an individual suffering a bacterial disease which comprises i) isolating the bacterium causing the bacterial disease from a sample originating from said individual, and ii) evaluating the integrity of the cell wall of said bacterium by means of a method according to the present invention, wherein if the integrity of the cell wall of said bacterium has been damaged, then said individual can receive a therapy based on an antibiotic acting on the cell wall.

In another aspect, the invention relates to a method for identifying a compound acting on the bacterial cell wall which comprises:

i) contacting a culture containing a bacterium sensitive to an antibiotic acting on the bacterial cell wall in the presence of the candidate compound, and ii) evaluating the integrity of the cell wall of said bacterium by means of a method according to the present invention, wherein if the integrity of the cell wall of said bacterium has been damaged, then the candidate compound is a compound acting on the bacterial cell wall.

In another aspect, the invention relates to a method for identifying a persister bacterium or a bacterium tolerant to an antibiotic acting on the bacterial cell wall in a culture containing sensitive bacteria, which comprises evaluating the integrity of the cell wall of the bacteria present in said culture by means of a method according to the present invention, wherein the bacterium the cell wall integrity of which has not been damaged is identified as a persister or tolerant bacterium.

In another aspect, the invention relates to a lysis solution characterized in that it only affects the bacteria having the bacterial wall damaged by the action of an antibiotic, comprising a buffer and a pH between 3 and 11.5.

In another aspect, the invention relates to the use of the lysis solution of the present invention for evaluating bacterial cell wall integrity.

In another aspect, the invention relates to a kit comprising the lysis solution of the invention.

DETAILED DESCRIPTION OF THE INVENTION

Figure 1:
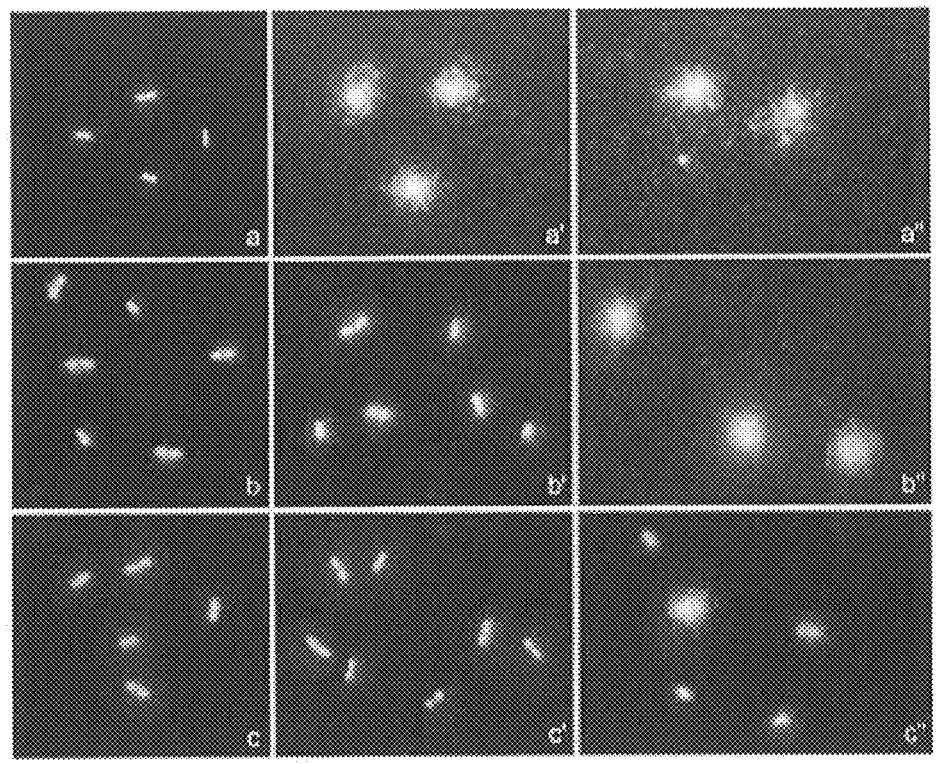
FIG. 1 shows three different strains of *Escherichia coli*, a Gram− bacterium, that are exposed to β-lactam antibiotic, amoxicilin, together with beta-lactamase inhibitor, clavulanic acid, processed by means of the technique for evaluating cell wall integrity. The incubation was in Mueller-Hinton liquid medium during the exponential growth phase at 37° C. with stirring for 40 minutes. The doses of antibiotic were chosen according to the cutoff points indicated by the Clinical and Laboratory Standards Institute (CLSI). Therefore, the strain is considered sensitive when its minimum inhibitory concentration (MIC) is ≤8/4 (8 µg/mL amoxicilin and 4 µg/mL clavulanic acid) and resistant when its MIC is ≥32/16 (32 µg/mL amoxicilin and 16 µg/mL clavulanic acid). According to standard microbiology techniques, the first strain (top row: a, a', a") is a sensitive strain, the second strain is a strain with intermediate sensitivity (middle row: b, b', b") and the third strain is a resistant strain (bottom row: c, c', c"). a, b, c: antibiotic-free control. a', b', c': 8/4; 8 µg/mL amoxicilin and 4 µg/mL clavulanic acid; a", b", c": 32/16; 32 µg/mL amoxicilin and 16 µg/mL clavulanic acid. The antibiotic-free controls (a, b, c) show the non-lysed bacteria. After a dose of 8/4, only the bacteria of the first sensitive strain are lysed, showing the nucleoids (a'). After a dose of 32/16, the first sensitive strain and second strain with intermediate sensitivity are lysed (a" and b"), whereas the third resistant strain is not lysed (c"). However, some cell wall damage is visible in some isolated cells. When the antibiotic is effective, in addition to the release and spread of nucleoids, a diffused homogeneous microgranular background containing DNA fragments given off by the cells is observed.

Based on the discovery mentioned in the section relating to the Description of the Invention, the inventors have developed a series of inventive aspects that will be explained in detail below.

Methods for Evaluating Bacterial Cell Wall Integrity of the Invention

In one aspect, the invention relates to a method for evaluating the integrity of the cell wall of a bacterium in a pure culture in the presence of an antibiotic acting on the bacterial cell wall (hereinafter, "first method of the invention"), which comprises:

i) adding to said pure culture of said bacterium an antibiotic acting on the bacterial cell wall, and ii) determining the presence of extracellular DNA fragments in the culture medium, wherein the presence of extracellular DNA fragments in the culture medium is indicative that the integrity of the cell wall of the bacterium has been damaged.

In the context of the present invention, the term "cell wall" refers to the cell wall enveloping a bacterial cell which is made up of murein peptidoglycan, that is formed by an alternating sequence of N-acetylglucosamine (NAG) and N-acetylmuramic acid (NAM) bound to one another by means of $\beta$-1,4 bonds. The terms "cell wall" and "bacterial cell wall" are equivalent and can be used interchangeably throughout the present description.

In the present invention, "evaluating the integrity of the cell wall of a bacterium" is understood as the action of determining if the original components or structure of the bacterial cell wall have been damaged, or if in contrast, its components and structure remain intact after the exposure to a foreign agent. In the context of the present invention, the foreign agent is an antibiotic acting on the bacterial cell wall, i.e., an antibiotic that blocks peptidoglycan synthesis such that the cell wall of the bacterium is damaged.

In the present invention, "pure culture" is understood as any culture containing a single type of microorganism. The different culture media, techniques and methods for obtaining pure cultures are widely known in the state of the art and are routine practice for the person skilled in the art (Rotger, R. (editor), 1997, Microbiologia Sanitaria y clinica, Editorial Sintesis, Madrid).

The first step of the first method of the invention [step i)] comprises adding to said pure culture of said bacterium an antibiotic acting on the bacterial cell wall.

The term "antibiotic" includes any chemical compound which eliminates or inhibits the growth of infectious organisms; as used herein, said term includes any chemical compound produced by a living being, or a synthetic derivative thereof, which eliminates or inhibits the growth of infectious organisms at low concentrations. A property common to all the antibiotics is the selective toxicity: toxicity is greater for invading organisms than for animals or human beings hosting them. Antibiotics can be classified according to their structure, the microorganism to which they attach, to their mechanism of action, to their therapeutic target, etc. In the present invention, "antibiotic acting on the bacterial cell wall" is understood as an antibiotic which interferes in any of the steps of bacterial wall synthesis. A test for determining if an antibiotic acts on the cell wall is, for example, any of the tests described in the examples of the present patent application.

In a particular embodiment, the antibiotic acting on the bacterial cell wall is selected from the group consisting of a $\beta$-lactam antibiotic, an isoniazid, an ethionamide, an ethambutol, a cycloserine and a glycopeptide antibiotic.

In another particular embodiment, the $\beta$-lactam antibiotic is selected from the group consisting of penicillins, cephalosporins, cephamycins, carbacephem, carbapenems, monobactams and $\beta$-lactamase inhibitors.

In another particular embodiment, the β-lactamase inhibitors are selected from the group consisting of clavulanic acid, sulbactam and tazobactam.

In another particular embodiment, the glycopeptide antibiotic is vancomycin or teicoplanin.

As is known by the person skilled in the art, the incubation time of the culture together with the antibiotic can vary within a wide range depending on whether the culture is in a stationary or exponential growth phase, on whether the culture is carried out on a dish or in a liquid medium, on the dose of antibiotic which is added to the culture, etc. Generally, the incubation time with the antibiotic can range from 5 minutes to 90 minutes, preferably from 20 to 60 minutes. In a particular embodiment, the incubation time is 10, 15, 20, 25, 30, 35, 40, 45, 50, 55, 60, 65, 70, 75 or 80 minutes. In addition, the amount of antibiotic to be added to the culture medium can also vary within a wide range; nevertheless, in a particular embodiment, the amount of antibiotic to be added to the culture medium is comprised between 5 and 2,570 µg/mL, although preferably, the amount of antibiotic to be added will be the minimum inhibitory concentration (MIC) for a specific bacterium. As is known by the person skilled in the art, in the state of the art there are widely accepted standardized tables where the MIC necessary for inhibiting a specific microorganism is listed. In a particular embodiment, the amount of antibiotic that can be added to the culture medium is 0.06, 0.038, 0.38, 4, 8, 16, 20, 32, 160, 256 or 2,560 µg/mL. Finally, the incubation temperature of the culture with the antibiotic can range between 36° C. and 38° C., preferably 37° C.

The second step of the first method of the invention [step ii)] comprises observing the presence of extracellular DNA fragments in the culture medium.

As is understood by the person skilled in the art, the presence of DNA fragments in the medium can be determined by microscopy or by any other alternative physical or chemical method for detecting DNA released into the culture medium by the microorganisms including, without limitation, electrophoresis, antibodies, spectrophotometry, polymerase chain reaction, hybridization techniques, microarrays, microfluidics, nanoparticles, quantum dots, etc. These methods are widely known in the state of the art and putting the methods into practice is a routine practice for the person skilled in the art.

Nevertheless, due to the relatively small size of the DNA fragments, in a particular embodiment, microscopy is the technique of choice for determining the presence of DNA fragments given its higher sensitivity. To that end, it is suitable to immobilize a sample from the culture resulting from the first step [step i)] on a slide. Therefore, in a particular embodiment, the first method of the invention comprises performing, between steps i) and ii), the step of immobilizing a sample from the culture of step i) on a support.

Said support can be a slide. In a particular embodiment, said slide is a glass slide completely or partially coated with a standard agarose film. To that end, a standard agarose solution between 0.2 and 1% in distilled water is prepared in a Coplin jar or the like; it is covered with a perforated plastic sheet and deposited in a microwave oven; the microwave oven is adjusted to a power comprised between 300 W and 1000 W, preferably to 500 W, stirring the container occasionally for a better agarose dissolution, leaving it to boil. This method can also be carried out using a thermostatic bath. When the agarose solution becomes completely transparent, it will be ready to be deposited in vertical vessels with a content between 10 and 250 ml. These vessels must be previously tempered in a bath between 60-100° C., preferably at 70° C., to maintain the agarose solution in liquid state. The clean slides are then submersed vertically, holding them with tweezers by the ground area between 1 and 60 seconds, removing them and submersing them again between 1 and 10 times, until forming a homogeneous film on the slide. Alternatively, instead of submersing the slide in the agarose solution, it is possible to use a sprayer, dispersing the agarose on the slide. A large amount of slides can thus be coated in a short time period. Regardless of the method used, the slides coated with an agarose film are deposited horizontally on a smooth and cold surface between 1 and 15° C., preferably at 4° C., made of glass or metal, for example. This plate with the slides is introduced in the refrigerator at 4° C. for at least 30 minutes, until verifying that the agarose solution has gelled on the surface of the slide. The trays are removed from the refrigerator and the surface of the slides which was in contact with the dish is cleaned with blotting paper. The slides are then introduced horizontally in an oven at a temperature comprised between 37° C. and 100° C., until the agarose has dried completely and forms a fine film adhered to the glass. The slides thus treated can be used immediately or stored in a well closed case at room temperature for several months.

The immobilization of a sample from the culture of step i) on a slide prepared in the manner explained above, requires the prior preparation of said sample. By means of the conventional methods in this field, the concentration of microorganisms in a liquid sample is obtained and verified. The concentration suitable for the analysis ranges between 0.1 and 20 million of microorganisms per milliliter. If the sample were too concentrated, it is adjusted to the suitable concentration by diluting it with culture medium or with saline/phosphate buffered solution (PBS) or the like, suitable according to the microorganism and according to the stability of the antibiotic to be tested.

To facilitate the processing of the sample containing the microorganisms, it is introduced in a medium with characteristics similar to those of a suspension, such as an agarose microgel, for example. In this case, a low melting/low gelling point agarose solution is prepared at a concentration comprised between 0.5 and 3% in distilled water or phosphate buffered saline (PBS). This agarose is melted using a microwave oven or a thermostatically controlled bath, and is subsequently maintained between 30 and 37° C. in a tube introduced in a thermostatically controlled bath or an oven. The sample from the culture and the agarose solution are carefully mixed in an Eppendorf tube or the like, such that the latter is at a concentration comprised between 0.3 and 2%, for example, 70 µL of agarose solution+30 µL of sample. It is important for the temperature of the agarose to not exceed 37° C. to prevent damaging the microorganisms.

Finally, to obtain the sample on the support, the slides coated with agarose are placed on a smooth and cold glass or metal surface, with a temperature comprised between 1 and 15° C., preventing the formation of air bubbles. It is recommended to deposit a drop (between 2 and 200 microliters (µL)) of the mixture (prepared sample from the culture+agarose) with a micropipette, placing a cover slip on top of the drop. Several drops, i.e., samples from bacterial culture of step i), can be pipetted on each slide. As a precaution, it is recommended to process each sample in duplicate and to use a control sample every time the technique is applied. The dish with the slides is introduced in a refrigerator at 4° C. for a time period comprised between 2 to 30 minutes until a suitable gelling of the agarose occurs.

Once the gelling has occurred, the cover slips are gently removed inside the same refrigerator, preventing damaging the microgel.

Subsequently, to view the DNA fragments by microscopy, it is suitable to stabilize and firmly adhere the DNA fragments on the slide since they may become detached. To that end, the dry slides are incubated in a microwave oven at a power comprised between 300 W and 1000 W, preferably at 500 W, for a time period comprised between 1 and 10 minutes. An alternative, although less recommendable due to its duration, is to incubate the slides in a furnace or an oven at a high temperature for a time period comprised between 1 and several hours. Once they are completely dry, the already processed slides containing the sample can be stored in filing cases at room temperature in the dark for months. This facilitates separating the sample treatment process and the subsequent step of evaluating the integrity of the cell wall of the microorganisms. The filing allows a repeated evaluation at different intervals of several samples of one and the same microorganism.

Once the samples are treated and after the DNA fragments are stabilized and firmly adhered to the slides, the samples can be stained and the integrity of the cell wall of the microorganisms can be evaluated. Therefore, in a particular embodiment of the method of the invention the observation of the presence of extracellular DNA fragments in the culture medium is carried out by means of staining. A high image quality and a high evaluation result consistency can be obtained by suitably choosing the staining conditions.

Staining or dyeing is an auxiliary technique in microscopy to improve contrast in the image seen through a microscope. In biochemistry, this means adding a specific dye for the molecule to be stained (DNA in the context of the present invention) to a substrate for qualifying or quantifying the presence of a specific compound. Stains can be used, among other purposes, for defining and examining organelles in individual cells or for labeling nucleic acids in gel electrophoresis.

Most dyes are organic compounds having some specific affinity for cellular materials. Many frequently used dyes are positively charged molecules (cations) that intensively combine with the negatively charged cellular constituents, such as nucleic acids and acidic polysaccharides. Non-limiting illustrative examples of cationic dyes include methylene blue, crystal violet and safranin. Methylene blue is a good simple dye that acts rapidly on all bacterial cells and does not produce a color so intense that it obscures the cellular details, which is particularly useful. Occasionally, some dyes stain better only after the cell has been treated with another chemical substance known as a mordant which is not a dye per se. Tannic acid is a common mordant that combines with a cellular constituent and alters same such that it can now attack the dye. As is known by the person skilled in the art, there are techniques in the state of the art specific for staining DNA, such as for example, Feulgen staining which consists of subjecting the material to a hydrolysis with 1 N hydrochloric acid at 60° C. or with 5 N hydrochloric acid at room temperature and then adding the Schiff reagent. It is possible to stain the nuclei of the bacterial cells by means of this technique.

As indicated above, due to the relatively small size of the DNA fragments, in a particular embodiment, fluorescence microscopy is the technique of choice for viewing the DNA fragments given its higher sensitivity, to that end the bacteria must be stained with specific chemical compounds called fluorophores or fluorochromes. These compounds are capable of emitting fluorescence when they are excited with light at a suitable wavelength. Today there is an entire range of fluorochromes that do not only provide information about cell viability, but also clearly show certain physiological characteristics and in some cases structural characteristics of bacteria. By way of illustration, there are fluorophores which detect respiratory activity (e.g., tetrazolioum derivatives, etc.), esterase activity (e.g., calcein-AM, carboxyfluoresceine, etc.), membrane potential (e.g., rhodamine 123, oxonol VI, carbocyanines, etc.), membrane integrity (e.g., SYTO-9, SYTO-13, Sytox green, propidium iodide, etc.), etc.

Therefore, in a particular embodiment the staining is carried out by means of using one or more fluorochromes. Therefore, depending on the availability of fluorescence filters, the samples can be stained with DNA-specific fluorochromes of the DAPI (4',6-diamidino-2-phenylindole) type, Hoechst 33258 type, Hoechst 33342 type, ethidium bromide type, propidium iodide type, etc. However, fluorochromes having higher sensitivity, such as GelRed, EvaGreen, and other cyanine derivatives, such as SYBR®, PicoGreen® (Invitrogen-Molecular Probes™) families, the variants of TOTO, YOYO, BOBO, POPO, JOJO, LOLO, SYTOX, PO-PRO, BO-PRO, YO-PRO, TO-PRO, JO-PRO, PO-PRO, LO-PRO, etc., are preferred. Other types of fluorochromes include, but are not limited to, SYTOX blue, chromomycin A3, mithramycin, acridine orange, SYTOX green, thiazole orange, LDS 751, 7-AAD, SYTOX orange, DRAQ5.

In a particular embodiment, the fluorochromes are selected from the group consisting of Hoechst 33342, Hoechst 33258, DAPI, chromomycin A3, mithramycin, ethidium bromide, acridine orange, thiazole orange, 7-AAD, cyanine derivatives, and the variants of fluorochromes TOTO, YOYO, BOBO, POPO, JOJO, LOLO, SYTOX, PO-PRO, BO-PRO, YO-PRO, TO-PRO, JO-PRO, PO-PRO and LO-PRO The amount and quality of fluorochromes is currently increasing. To prevent the loss of fluorescence, an antifading medium (for example Vectashield-Vector H-1000, DABCO; etc.) can be included. However, these media usually cause diffuse fluorescence and a light background making the contrast of the image difficult. Therefore, it is generally preferable to use a highly sensitive and relatively photostable fluorochrome, mounted in an aqueous buffered solution, and to evaluate the sample relatively quickly, before it dries. If necessary, the slide can be washed and stained again.

The images obtained can be studied by means of direct visual analysis or, preferably, by applying software for analyzing digitized images obtained by means of analog or digital cameras coupled to microscopy platforms.

Finally, the integrity of the wall of the microorganisms is evaluated by means of determining the presence of extracellular DNA fragments in the culture medium, wherein the presence of extracellular DNA fragments in the culture medium is indicative that the integrity of the cell wall of the bacterium has been damaged.

Nevertheless, as mentioned above (Description of the Invention), when the bacterial culture is a mixed or a contaminated culture, i.e., there is a mixture of cells that are sensitive or resistant to the antibiotics acting on the bacterial cell wall, the first method of the invention would not be very suitable as a strict discrimination criterion because both the bacteria sensitive and resistant to the antibiotic show an apparently intact cell wall. To solve this problem, the inventors have designed a lysis solution that only affects the bacteria the cell wall of which has been previously damaged by the action of the antibiotic acting on the cell wall. This lysis solution can be added to the bacterial culture which has been previously exposed to the action of said antibiotic, the bacterial nucleoid being released and a bacterium with damaged cell wall then being then observed (Examples 1 to 5). Therefore, the presence of bacterial nucleoid after applying the lysis solution is indicative of the presence of bacteria sensitive to said antibiotic acting on the cell wall.

Therefore, in another aspect the invention relates to a method for evaluating the integrity of the cell wall of the bacteria present in a culture in the presence of an antibiotic acting on the bacterial cell wall (hereinafter, "second method of the invention"), which comprises:
i) adding to said culture an antibiotic acting on the bacterial cell wall,
ii) adding lysis solution to the culture resulting from step i), wherein said lysis solution is a lysis solution specific for those bacteria the cell wall of which has been damaged by the antibiotic acting on the bacterial cell wall, and comprises a buffer with a pH comprised between 3 and 11.5, and
iii) determining the presence of bacterial nucleoid,
wherein the presence of bacterial nucleoid in the medium is indicative that the integrity of the cell wall of the bacteria has been damaged.

The terms and expressions "evaluating the integrity of the cell wall of bacteria", "cell wall" and "antibiotic acting on the cell wall" have already been defined above in the first method of the invention, and are applicable to the present inventive aspect.

In addition, although the second method of the invention has been designed for evaluating the integrity of the cell wall of bacteria in a mixed or contaminated culture, the person skilled in the art understands that said second method of the invention can also apply to pure cultures.

The term "pure culture" has been defined above in the present description. In the present invention, a "mixed culture" is understood as a bacterial culture containing two or more different species of bacteria. In most cases, the presence of two or more different species of bacteria in a culture results from the contamination of the culture due to incorrect sample handling, so in the context of the present invention, the terms "mixed culture" and "contaminated culture" are equivalent and can be used interchangeably throughout the description. Therefore, in a particular embodiment of the second method of the invention the bacteria present in the culture belong to the same species or to different species.

As can be seen by the person skilled in the art, steps i) and iii) of the second method of the invention are common to the first method of the invention [steps i) and ii), respectively]. Therefore, all the explanations and particular embodiments previously mentioned in relation to said steps also apply to the second method of the invention.

The second method of the invention comprises, in addition to steps i) and iii) [common to steps i) and ii) of the first method of the invention], a step ii) not found in the first method of the invention which comprises adding a lysis solution to the culture resulting from step i), wherein said lysis solution is a lysis solution specific for those bacteria the cell wall of which has been damaged by the antibiotic acting on the bacterial cell wall, and comprises a buffer with a pH comprised between 3 and 11.5.

The lysis solution specifically affecting bacteria having the cell wall affected by the antibiotic acting on the bacterial cell wall basically comprises a buffer solution which has a pH between 3 and 11.5 but which can additionally comprise other components including, but not limited to, ionic detergents, non-ionic detergents, salts, etc. at different proportions.

Therefore, in a particular embodiment the buffer which is part of the lysis solution is tris(hydroxymethyl)aminomethane (Tris) with formula $(HOCH_2)_3CNH_2$ that can also be used for preparing other buffer solutions including, but not limited to, Tris-HCl buffer, Tris-Gly buffer, TAE (Tris-acetate-EDTA) buffer and TBE (Tris-borate-EDTA) buffer. The Tris has a pKa of 8.06 which provides it with effective buffering capacity at a range of pH comprised between 7.0 and 9.2. The most frequently used form is called Tris base (the non-ionized basic form of amine); the acid form or hydrochloride (Tris-HCl) is also used sometimes. Other buffer solutions include, but are not limited to, Hepes, Mops, Pipes, etc. To obtain a stable pH close to 11.5, dibasic sodium phosphate also known as disodium hydrogen phosphate ($Na_2HPO_4$), boric acid-borate, triethylamine and 4-[cyclohexylamino]-1-butanesulfonic acid (CABS) are used.

In another particular embodiment, the lysis solution comprises, in addition to the buffer solution, up to 3% of an ionic detergent or of a non-ionic detergent.

As used herein, the term "ionic detergent" refers to any compound having a hydrophobic portion and a hydrophilic portion, which forms positively charged ions (cationic detergent) or negatively charged ions (detergent anionic) in solution and which allows obtaining an emulsion. As is understood by the person skilled in the art, the terms "detergent", "surfactant" and "surface active agent" are synonyms, so they can be used interchangeably throughout the present description.

Examples of cationic detergents include, but are not limited to, primary, secondary, tertiary and quaternary ammonium salts with linear or cyclic structure, mixtures thereof, such as for example, pyridine salts, piperazine salts, and derivatives of said ammonium salts. The term "derivatives of ammonium salts" includes those salts incorporating in the same structure at least two primary, secondary, tertiary and/or quaternary amino groups, such as for example, guanidine, piperazine and imidazole salts. This definition would also comprise amino acid salts, such as for example, lysine, arginine, ornithine or tryptophan salts. Likewise, this definition would encompass ammonium salts in which the positive charge, instead of being on the nitrogen atom, is on a phosphorus atom, such as for example, ditetradecyl(trimethylethylphosphonio) methylphosphonate iodide, ditetradecyl(butyldimethylphosphonio) methylphosphonate iodide, ditetradecyl (dimethylisopropylphosphonio iodide) methylphosphonate iodide or arsenic ditetradecyl (trimethylarsonio) methylphosphonate iodide, dioleyl (trimethylphosphonio) methylphosphonate iodide. Examples of ammonium salts include, but are not limited to, tetraalkylammonium salts, alkylbenzyl-dimethyl-ammonium salts or heterocyclic ammonium salts, such as cetyltrimethylammonium bromide (CTAB).

Non-limiting illustrative examples of ionic detergents include acyl-amino acids, such as acyl-glutamic acids, acyl-peptides, sarcosinates, taurates, etc., carboxylic acids, such as acids with saturated chain, carboxylic acid esters, carboxylic acid ethers, phosphoric acid esters, sulfonic acids, such as acyl-isothianates, alkyl aryl sulfonates, alkyl sulfonates, sulfosuccinates, etc., and sulfuric acid esters, such as alkyl ether sulfates and alkyl sulfates.

In a particular embodiment, the ionic detergent is a detergent selected from the group consisting of sodium dodecylsulfate (SDS), alkylbenzene sulfonate, laurylsarcosine, glycocholic acid salt hydrate, and the salts thereof.

Examples of non-ionic detergents include, but are not limited to, polysorbates, polyethylene glycol copolymers and polypropylene glycol copolymers, such as for example Tween, Span, Poloxamer.

In another particular embodiment, the non-ionic detergent is selected from the group consisting of t-octylphenoxypolyethoxyethanol, N,N-Bis(3-D-gluconamidopropyl)cholamide, Brij(r) 35 P, N-decanoyl-N-methylglutamine, digitonin, dodecanoyl-N-methylglucamide, heptanoyl-N-methylglutamide, branched octylphenoxypoly(ethyleneoxy)ethanol, N-nonanoyl-N-methylglucamine, Nonidet P 40, N-octanoyl-N-methylglutamine, Span 20 solution and polysorbate 20.

In another particular embodiment, the lysis solution further comprises up to 3 M concentration of a salt. Examples of salts that can be part of the lysis solution of the invention include, but are not limited to, carbonates, chlorides, phosphates, nitrates, nitrites, sulfates, citrates, carboxylates (acetates, formates, salicylates, etc.). In a particular embodiment, the lysis solution comprises sodium chloride (NaCl).

In a particular embodiment, the lysis solution provided by this invention comprises between 0.001 M and 2 M Tris, up to 3% SDS and NaCl up to a concentration of 3 M, at a pH comprised between 3 and 11.5. Nevertheless, the person skilled in the art will understand that these compounds can be replaced with other equivalent compounds; for example, SDS can be replaced with up to 10% Triton X-100.

In another particular embodiment, the lysis solution provided by this invention comprises about 0.2 M (hydroxymethyl)-1,3-propanediol (Tris), about 0.025% SDS, about 0.5 M or 0.05 M sodium chloride, and pH 10; in this case, the SDS can be replaced with about 5% Triton X-100.

In another particular embodiment, the lysis solution provided by this invention comprises about 0.2 M (hydroxymethyl)-1,3-propanediol, about 5% Triton X-100, about 1 M sodium chloride, and pH 10.

In another particular embodiment, the lysis solution provided by this invention comprises about 0.3 M dibasic sodium phosphate, about 2% SDS, about 0.05 Methylenediamine-tetraacetic acid (EDTA) and pH 11.45.

According to the solution used and the type of sample, the preparations are incubated in the lysis solution between 0.5 and 120 minutes, preferably between 1 and 35 minutes, more preferably for about 5 minutes; and at a temperature comprised between 1° C. and 45° C., preferably between 15° C. and 40° C., more preferably between 22° C. and 37° C. In a particular embodiment, the incubation is carried out at a temperature of 22° C. In another particular embodiment, the incubation is carried out at a temperature of 37° C.

Once the lysis solution is added to the bacterial culture previously incubated in the presence of an antibiotic acting on the cell wall, the presence of bacterial nucleoid in the culture medium is detected [step iii)]. As described for the first method of the invention, the evaluation of the presence of bacterial nucleoid in the medium can be performed by microscopy or by any other alternative physical or chemical method for detecting the DNA released by the microorganisms into the culture medium including, without limitation, electrophoresis, antibodies, spectrophotometry, polymerase chain reaction, hybridization techniques, microarrays, microfluidics, nanoparticles, quantum dots, etc. These methods are widely known in the state of the art and putting the methods into practice is a routine practice for the person skilled in the art.

Nevertheless, in a particular embodiment, the detection of the bacterial nucleoid is carried out by means of microscopy, for which it is necessary to immobilize a sample from the culture resulting from step i) [i.e., after exposing the bacterial culture to the action of the antibiotic] on a support such as a slide, for example. In this case, step ii) of the second method of the invention, i.e., the addition of the lysis solution that only affects the bacteria the cell wall of which has been affected by the antibiotic, can be carried out before or after immobilizing the bacteria on said support. Therefore, in a particular embodiment the second method of the invention further comprises immobilizing a sample from the culture on a support before or after step (ii). The methods and techniques existing in the state of the art for immobilizing samples on supports, as well as for preparing same have already been described above in relation to the first method of the invention and they apply to the second method of the invention.

If the treatment with the lysis solution is performed after immobilizing a sample from the culture resulting from step i) on a support, such as a slide, said slide is submersed in a horizontal position in a vessel containing the lysis solution. After the treatment with the lysis solution (discussed above), the preparations can be washed to remove the rest of this solution. To that end, the supports are introduced in a washing solution that is as mild as possible, avoiding chelating agents or detergents; by way of illustration, the supports can be submersed in a horizontal position in a vessel containing a lot of distilled water or a buffer solution or physiological serum for a time between 1 and 60 minutes.

Thereafter, the sample is dehydrated. To that end, solutions with increasing alcohol concentration can be used. By way of example, the slides are lifted and submersed in vessels with a series of increasing ethanol concentration, between 5% and 100%, for 30 seconds to 60 minutes each and the preparations are then allowed to air dry. The temperature of the alcohols can range from −20° C. to room temperature. It can be preferable to use alcohols at −20° C. to improve DNA precipitation, for 5 minutes each. As alternatives to the incubations in a series of ethanol, the preparations can be dehydrated by incubating in solutions of different alcohols such as methanol, or allowing to air dry or to dry in an oven.

Finally, the presence of bacterial nucleoid in the culture medium or on the support if the sample has been immobilized is determined in step iii) of the second method of the invention.

In the present invention, "bacterial nucleoid" is understood as the region containing DNA in the cytoplasm of bacterial cells. The experimental evidence suggests that nucleoid is essentially made up of DNA (60%), with small proportions of RNA and proteins. These last two components act as messenger RNA and as genome regulatory proteins. In the state of the art, bacterial nucleoid is also known as "nuclear region" or "nuclear body". The techniques for observing the presence of extracellular DNA fragments in the culture medium described above can also be used for observing bacterial nucleoid as required in the second method of the invention.

If the technique of choice for determining the presence of bacterial nucleoid is microscopy, then, as described above in the first method of the invention, it is suitable to stabilize and firmly adhere the DNA fragments to the slides since they can become detached.

Once the samples are treated and after the DNA fragments are stabilized and firmly adhered to the slides, the samples can be stained and the integrity of the cell wall of the microorganisms can be evaluated. Therefore, in a particular embodiment of the second method of the invention, the observation of the presence of bacterial nucleoid in the culture medium is carried out by means of staining. A high image quality and a high evaluation result consistency can be obtained by suitably choosing the staining conditions. The different staining techniques as well as the dyes that can be used for viewing DNA by means of microscopy have been described above in the present description in relation to the first method of the invention and they apply to the second method of the invention.

Therefore, in a particular embodiment the observation of the presence of bacterial nucleoid in the culture medium is carried out by means of staining which, in a more particular embodiment, is carried out by means of using fluorochromes which, in another still more particular embodiment, are selected from the group consisting of Hoechst 33342, Hoechst 33258, DAPI, chromomycin A3, mithramycin, ethidium bromide, acridine orange, thiazole orange, 7-AAD (7-aminoactinomycin D), cyanine derivatives, variants of fluorochromes TOTO, YOYO, BOBO, POPO, JOJO, LOLO, SYTOX, PO-PRO, BO-PRO, YO-PRO, TO-PRO, JO-PRO, PO-PRO and LO-PRO, etc.

Putting the second method of the invention into practice requires, in a first step, adding to a bacterial culture an antibiotic acting on the bacterial cell wall. Any of the antibiotics described above in the first method of the invention can be used in the second method of the invention. Therefore, in a particular embodiment the antibiotic acting on the bacterial cell wall is selected from the group consisting of a β-lactam antibiotic (including, but not limited to, penicillins, cephalosporins, cephamycins, carbacephem, carbapenems, monobactams and β-lactamase inhibitors such as clavulanic acid, sulbactam, tazobactam, etc.), an isoniazid, an ethionamide, an ethambutol, a cycloserine and a glycopeptide antibiotic (including, without limitation, vancomycin or teicoplanin).

Applications of the Methods of the Invention

As described above, the practical application of the first and second method of the invention is to determine in a rapid and reliable manner if a bacterium is sensitive or resistant to an antibiotic acting on the bacterial cell wall. Evaluating the integrity of the bacterial wall by means of any of the methods of the invention described above in the present description is sufficient for that purpose.

Therefore, in another aspect the present invention relates to a method for determining the sensitivity of a bacterium to an antibiotic acting on the bacterial cell wall which comprises evaluating the integrity of the cell wall of said bacterium by means of any of the methods of the invention, wherein if the integrity of the cell wall of the bacterium has been damaged, then the bacterium is sensitive to the antibiotic. In contrast, as is understood by the person skilled in the art, if the integrity of the cell wall has not been damaged and it is intact (there is no release of extracellular DNA fragments or nucleoid into the culture medium), then the bacterium is not sensitive to the antibiotic, the bacterium can be a resistant bacterium or a bacterium called a persister or tolerant bacterium. Both types of bacteria are not affected by the antibiotic acting on the bacterial cell wall, but they are different in that resistant bacteria have DNA mutations such that the antibiotic resistance is permanent, whereas the persister bacteria have no DNA mutations for resistance, it being a reversible functional state. Therefore, other applications of the methods of the invention consist of detecting resistant bacteria or persister bacteria in a sample.

Therefore, in another aspect the invention relates to a method for identifying a persister bacterium or a bacterium tolerant to an antibiotic acting on the bacterial cell wall in a culture containing sensitive bacteria, which comprises evaluating the integrity of the cell wall of the bacteria present in said culture by means of the second method of the invention, wherein the bacterium the cell wall integrity of which has not been damaged is identified as a persister or tolerant bacterium.

Another practical application of the methods of the invention relates to the design of an antibiotic therapy customized for an individual suffering from a bacterial disease, because whether the bacterium causing the bacterial disease is sensitive or resistant to a specific antibiotic can be determined by means of the methods of the invention. If after applying any of the methods of the invention the bacterium causing the bacterial disease is found to be sensitive to the tested antibiotic, then the physician can make a decision to administer a therapy based on said antibiotic to the individual suffering said bacterial disease. If in contrast the bacterium causing the bacterial disease is resistant to the tested antibiotic, then the physician will choose a treatment that is not based on said antibiotic.

Therefore, in another aspect the present invention relates to a method for designing an antibiotic therapy customized for an individual suffering a bacterial disease which comprises
  i) isolating the bacterium causing the bacterial disease from a sample originating from said individual, and
  ii) evaluating the integrity of the cell wall of said bacterium by means of any one of the methods of the invention,
wherein if the integrity of the cell wall of said bacterium has been damaged, then said individual can receive a therapy based on antibiotics acting on the cell wall.

In the present invention, "individual" is understood as a member of any animal species including, but not limited to, mammals, particularly, bovine livestock (cows, bulls, oxen, yaks, etc), ovine livestock (sheep, etc.), porcine livestock (pigs, wild boars, etc.), caprine livestock (goats, etc.), horselike or equine livestock (horses, mares, zebras, etc.), camelids (camels, llamas, alpacas, etc.), rabbits, hares, bisons, buffaloes, deers, reindeers, caribou, dogs, cats, mice, nonhuman primates (chimpanzees, gorillas, orangutans, macaques, gibbons, etc.). Particularly, the mammal is preferably a human being of any gender, age or race. The terms "individual" or "subject" are synonym and can be used interchangeably throughout the present description.

In the present invention, "bacterial disease" is understood as any disease resulting from bacterial infection on an individual. Examples of bacterial diseases include, without limitation, diseases caused by the infection of bacteria of genera *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Hemophilus* and *Bordetella*.

The first step of the method for designing an antibiotic therapy customized for an individual suffering a bacterial disease comprises isolating the bacterium causing said bacterial disease from a sample originating from said individual.

As is known by the person skilled in the art, a good sample selection, collection and transport, as well as a good sample processing for correct microorganism isolation are essential to ensure good results. For example, the sample must be representative of the infectious process and must be taken from the correct anatomical site, must be collected in sufficient amount to assure a suitable examination, sterile devices must be used during collection, etc. More information concerning the methods and materials used in sample collection can be found in Rotger, R. (editor), 1997 (mentioned ad supra).

In addition, antibiotics acting on the cell wall and can be administered to the individual depending on the conclusion reached have been described above in the present description.

The person skilled in the art will understand that the methods of the invention can also be used for identifying new antibiotic compounds acting on the cell wall. Therefore, in another aspect the invention relates to a method for identifying a compound acting on the bacterial cell wall which comprises:

i) contacting a culture containing a bacterium sensitive to an antibiotic acting on the cell wall in the presence of the candidate compound, and ii) evaluating the integrity of the cell wall of said bacterium by means of any of the methods of the invention, wherein if the integrity of the cell wall of said bacterium has been damaged, then the candidate compound is a compound acting on the bacterial cell wall.

In the present invention, "compound acting on the bacterial cell wall" is understood as a compound which interferes in any of the steps of bacterial cell wall synthesis or affects its structure.

The first step of the method for identifying compounds acting on the cell wall comprises contacting a culture of a bacterium sensitive to the antibiotics acting on the cell wall in the presence of the candidate compound. Examples of bacteria sensitive to the antibiotics acting on the cell wall include, but are not limited to, amoxicilin-sensitive strain of *E. coli*, ampicillin-sensitive strain of *Enterococcus faecalis*, iminepen-sensitive strain of *Acinetobacter baumannii*, ceftazidime-sensitive strain of *E. coli*, etc. More information concerning the sensitivity of bacteria to β-lactam antibiotics can be found in the state of the art (June 2010 CLSI Guidelines).

Lysis Solution of the Invention

The present invention is based on the fact that one consequence of the activity which the antibiotics acting on the cell wall have on bacteria is the release of extracellular DNA fragments into the culture medium. Additionally, when the bacterial culture is a mixed or contaminated culture, i.e., there is a mixture of sensitive or resistant cells, the observation of the extracellular DNA fragments would not be very suitable as a strict discrimination criterion because despite the release of extracellular DNA fragments, the morphology of the bacteria is not changed by the action of the antibiotic, i.e., both the bacteria sensitive and resistant to the antibiotic show an apparently intact cell wall. To solve this problem, the inventors designed a lysis solution that only affects the bacteria the cell wall of which has been previously damaged by the action of an antibiotic acting on the cell wall.

Therefore, another aspect of the present invention relates to a lysis solution, hereinafter lysis solution of the invention, characterized in that it only affects the bacteria having the bacterial wall damaged by the action of an antibiotic, comprising a buffer and a pH between 3 and 11.5.

The lysis solution specifically affecting bacteria having the cell wall damaged by the antibiotic acting on the bacterial cell wall basically comprises a buffer solution having a pH between 3 and 11.5 but which, as described in preceding inventive aspects, can additionally comprise other components, including, but not limited to, ionic detergents, non-ionic detergents, salts, etc. at different proportions.

Therefore, in a particular embodiment, the lysis solution of the invention further comprises up to 3% of an ionic detergent or a non-ionic detergent. In a specific embodiment, said ionic detergent is a detergent selected from the group consisting of sodium dodecylsulfate, alkylbenzene sulfonate, laurylsarcosine, glycocholic acid salt hydrate, and the mixtures thereof. In another specific embodiment, said non-ionic detergent is selected from the group consisting of t-octylphenoxypolyethoxyethanol, N,N-Bis(3-D-gluconamidopropyl)cholamide, Brij(r) 35 P, N-decanoyl-N-methylglutamine, digitonin, dodecanoyl-N-methylglutamide, heptanoyl-N-methylglutamide, branched octylphenoxypoly(ethyleneoxy)ethanol, N-nonanoyl-N-methylglutamine, Nonidet P 40, N-octanoyl-N-methylglutamine, Span 20 solution and polysorbate 20. In another specific embodiment, the lysis solution further comprises up to a 3 M concentration of a salt, for example, carbonates, chlorides, phosphates, nitrates, nitrites, sulfates, citrates, carboxylates (acetates, formates, salicylates, etc.); in a particular embodiment, the lysis solution comprises sodium chloride (NaCl).

In a particular embodiment, the lysis solution provided by this invention comprises between 0.001 M and 2 M Tris, up to 3% SDS, and up to 3 M concentration of NaCl, at a pH comprised between 3 and 11.5. Nevertheless, the person skilled in the art will understand that these compounds can be replaced with other equivalent compounds; for example, the SDS can be replaced with up to 10% Triton X-100.

In another particular embodiment, the lysis solution provided by this invention comprises about 0.2 M (hydroxymethyl)-1,3-propanediol (Tris), about 0.025% SDS, about 0.5 M or 0.05 M sodium chloride, and pH 10; in this case, the SDS can be replaced with about 5% Triton X-100.

In another particular embodiment, the lysis solution provided by this invention comprises about 0.2 M (hydroxymethyl)-1,3-propanediol, about 5% Triton X-100, about 1 M sodium chloride, and pH 10.

In another particular embodiment, the lysis solution provided by this invention comprises about 0.3 M dibasic sodium phosphate, about 2% SDS, about 0.05 M ethylenediamine-tetraacetic acid (EDTA) and pH 11.45.

More details and explanations concerning the different particular embodiments of the lysis solution of the invention can be found in the description of the second method of the invention.

In another aspect, the invention relates to the use of the lysis solution of the invention for evaluating bacterial cell wall. Information concerning how the lysis solution of the invention can be used for evaluating bacterial cell wall can be found in the description of the first and second methods of the invention.

Kit of the Invention

Putting the methods of the invention into practice requires a series of components that can be provided together in the form of a pack or kit, hereinafter kit of the invention. Useful components for putting the methods of the invention into practice include, but are not limited to, buffer solution, lysis solution, dyes, sterile material for sample collection (cotton swabs, swabs, tweezers, etc.), cover slips and slides, distilled water, alcohols (ethanol), etc. Additionally, the kit of the invention can contain instructions or indications guiding the person skilled in the art to put the methods of the invention into practice.

Therefore, in another aspect the invention relates to a kit comprising the lysis solution of the invention.

The following examples only illustrate the invention and are not meant to limit same.

EXAMPLES

Materials and Methods

Required Material and Equipment
Fluorescence microscope (immersion objective recommended)
Refrigerator at 4° C.
Oven at 37° C.
Oven or dish at 80° C. (optional)
Incubation bath at 37° C.
Plastic gloves
Glass cover slip (18×18 mm, 22×22 mm or 24×60 mm)
Micropipettes
4 cases for horizontal incubations
Distilled water
70%, 90%, 100% ethanol
Preparation of a Sample Per Slide
  1) Placing lysis solution in a covered horizontal incubation vessel in an oven at 37° C.
  2) Diluting the microorganism sample in a culture medium or PBS at a concentration of 5-10 million per milliliter.
Preparation of Agarose Microgel
  1) Introducing the Eppendorf tube with gelled agarose in the float, leaving it at the lid level, and leaving it to float for 5 minutes in water at 90-100° C. until the agarose melts. The agarose can alternatively be melted in a microwave oven.
  2) Transferring the Eppendorf tube with the float to a thermostatic bath at 37° C., and leaving it for 5 minutes until the temperature is balanced.
  3) Adding 60 µL of the microorganism sample to the content of the Eppendorf tube and resuspending with the micropipette.
  4) Placing a pretreated slide on a cold surface at 4° C. (for example, a metal or glass sheet).
  5) Once the slide is cold, depositing the microorganism suspension with agarose and placing a glass cover slip, preventing the formation of air bubbles. It is recommended to deposit a drop of 12, 20 or 50 microliters for a cover slip of 18×18 millimeters, 22×22 millimeters or 24×60 millimeters, respectively.
  6) Introducing the cold sheet with the slide in the refrigerator and leaving the sample to gel for 5 minutes.
Processing the Samples
  1) Removing the cover slip by sliding it gently using gloves, and immediately introducing the slide horizontally in the vessel with the lysis solution, covering and leaving to incubate for 5 minutes in the oven or bath at 37° C.
  2) Lifting the slide with the aid of a lancet using gloves. Holding the slide horizontally and depositing it horizontally in a case containing abundant distilled water or buffer solution to wash the lysis solution. Leaving to incubate for 5 minutes.
  3) Introducing the slide horizontally in a case with 70% ethanol (3 minutes), then in another case with 90% ethanol (3 minutes), and finally in 100% ethanol (3 minutes), at −20° C.
  4) Leaving it to air dry, and incubating in a microwave oven at 500-1000 W for 1-10 minutes, or in the absence thereof, in an oven at 80° C. for at least one hour or overnight. Once dry, the processed slides can be stored in filing cases at room temperature in the dark for months.

Staining of Samples for Observation Under a Fluorescence Microscope
  Depending on the availability of fluorescence filters, the samples can be stained with DNA-specific fluorochromes of the EvaGreen (green) or GelRed (red) type. The fluorochromes of the SYBR family, specifically SYBR Gold, allow good resolution with certain photostability.
Storage and Stability
  Store at room temperature.
  Shelf-life: the reagents and materials are stable for a period of at least 6 months. It is recommended to keep the lysis solution in a vertical position and well closed.
Determination of Cell Wall Integrity
  An aliquot of each sample was diluted to a concentration of 5-10 million of microorganisms/mL in Mueller-Hinton liquid medium, they were incubated with the antibiotic in Mueller-Hinton liquid medium. On the other hand, 0.5 mL microcentrifuge tubes containing gelled aliquots of low melting point agarose were placed in a water bath at 90° C.-100° C. for about 5 minutes to melt the agarose completely and then placed in a water bath at 37° C. Next, 25 µL of the diluted sample were added to said tubes and mixed with the molten agarose. An aliquot of 20 µL of the sample-agarose mixture was pipetted on a slide that had been previously coated (e.g., with an agarose film) and the sample was covered with a 22×22 mm cover slip. The slide was placed on a cold dish in a fridge (4° C.) for 5 minutes to allow the agarose to form a microgel with the intact cells trapped therein. The cover slip was carefully removed and the slide was immediately submersed in a horizontal position in a lysis solution for 5 minutes at 37° C. for Gram+ (gram positive) bacteria and at 22° C. for Gram− (gram negative) bacteria. The slide was washed horizontally on a tray with abundant distilled water for 3 minutes, it was dehydrated by incubating it horizontally in cold ethanol (−20° C.) at an increasing concentration (70%, 90% and 100%) for 3 minutes in each concentration and air dried in a furnace. The dry slide was incubated in a microwave oven at 750 W for 4 minutes and the DNA was stained with 25 µL of SYBR Gold (Molecular Probes, Eugene, Oreg., USA) diluted 1:400 in TBE buffer (0.09 M Tris-borate, 0.002 M EDTA, pH 7.5) for 2 minutes in the dark, with a glass cover slip. After a brief washing in pH 6.88 phosphate buffer (Merck, Darmstadt, Germany) a 24×60 mm cover slip was added and the slides were viewed by means of fluorescence microscopy.
Fluorescence Microscopy and Digital Image Analysis
  The images were viewed under an epifluorescence microscope (Nikon E800), with a 100× objective and fluorescence filters that are suitable for FITC-SYBR Gold (excitation at 465 nm, emission at 515-555 nm), PI-Cy3 (excitation at 540/25 nm, emission at 605/55 nm) and DAPI (excitation at 340-380 nm, emission at 435-485 nm). In the dose-response to ampicillin experiment, the images were captured with a high-sensitivity CCD camera (KX32ME, Apogee Instruments, Roseville, Calif., USA). Groups of 16-bit digital images were obtained and filed as .tiff files. The image analysis used a macro in the Visilog 5.1 program (Noesis, Gif sur Yvette, France). This allowed determining the threshold, subtracting the background and measuring the size of the mean width of the halo of the nucleoids in µm, demarcated between the peripheral end of the nucleoid and the outer limit of the cell body. In the case of unrecognized cell bodies, the centroid of the nucleoid was considered as the internal reference point for measuring the width of the halo of the scatterred nucleoid.

Example 1

Confirmation that the Technique Works: Release of Bacterial Nucleoid and of Diffused Wall Remains and/or Bacterial Products in Bacteria Sensitive to an Antibiotic Acting on the Bacterial Wall Three different strains of *Escherichia coli* were exposed to the β-lactam antibiotic, amoxicilin, together with the β-lactamase inhibitor, clavulanic acid, and processed by means of the technique for evaluating cell wall integrity of the present invention. The bacteria which were growing in Mueller-Hinton liquid medium were incubated with the antibiotic in Mueller-Hinton liquid medium for the exponential growth phase at 37° C., with stirring, for 40 minutes. The doses of antibiotic were chosen according to the cutoff points indicated by the Clinical and Laboratory Standards Institute (CLSI). According to its recommendations, a strain is considered sensitive when its minimum inhibitory concentration (MIC) is ≤8/4 (amoxicilin: 8 µg/mL and clavulanic acid: 4 µg/mL) and resistant when its MIC is ≥32/16 (amoxicilin: 32 µg/mL and clavulanic acid: 16 µg/mL). According to the disc diffusion data, one of the strains is a sensitive strain, another strain is a strain with intermediate sensitivity and the remaining strain is a resistant strain.

The results are shown in FIG. 1. After a dose of 8/4, only the bacteria of the sensitive strain are lysed, showing the nucleoids (a'). After a dose of 32/16, the sensitive strain and the strain with intermediate sensitivity are lysed (a" and b"), whereas the resistant strain is not lysed (c"). However, some cell wall damage is visible in some isolated cells. When the antibiotic is effective, in addition to the release and spread of nucleoids, a diffused homogeneous microgranular-fibrillar background of extracellular DNA fragments given off by the cells is observed.

Example 2

Assessment of β-Lactam Antibiotic Sensitivity or Resistance in Several Strains of *E. coli* Isolated from a Hospital Following the results of the preceding experiment (Example 1), 11 different strains of *E. coli* isolated in a Microbiology Service were studied. After growing on a dish with Mueller-Hinton medium for 24 hours, they were exposed to amoxicilin together with clavulanic acid in Mueller-Hinton liquid medium for 1 hour, after which they were processed by means of the technique for evaluating cell wall integrity according to the present invention. Like in Example 1, the doses were 0, 8/4 and 32/16 (amoxicilin/clavulanic acid).

According to the protocol of the invention:
Three strains showed complete wall lysis and an intense background of extracellular DNA fragments even at a low dose (8/4), these strains being categorized as sensitive strains.
5 strains only showed complete wall lysis and an intense background of extracellular DNA fragments at a high dose (32/16), these strains being considered as strains with intermediate sensitivity.
Two strains showed non-lysed cells along with other moderately lysed cells, with a very faint background or the absence of background of extracellular DNA fragments at a high dose. These strains were categorized as resistant strains.

The results of the technique were consistent with those provided by the Microbiology Laboratory.

The practical conclusion of the experiment is that the sensitive strains can be clearly distinguished from the rest using a single dose, specifically the low dose (8/4). This can greatly simplify the extensive study of multiple strains, since from the clinical point of view, what is important for making a therapeutic decision is to distinguish "sensitive" from "not sensitive". In the case of a strain with intermediate sensitivity to a specific antibiotic, said antibiotic would not be administered and other alternative antibiotic to which the strain is completely sensitive would be used.

Example 3

Determination of the Minimum Incubation Time with a β-Lactam Antibiotic that Allows Detecting an Effect on the Wall in the Sensitive Strain and the Strain with Intermediate Sensitivity of *E. coli*. Assessment of Bacteria Originating from Dish Culture or From Liquid Culture A sensitive strain, a strain with intermediate sensitivity and another resistant strain of *E. coli* were exposed to amoxicilin together with clavulanic acid in Mueller-Hinton liquid medium and processed by means of the technique for evaluating cell wall integrity of the present invention. The doses (amoxicilin/clavulanic acid) were: 8/4 (low) and 32/16 (high). The incubation times with the antibiotic were 5, 10, 20, 30, 40, 60 and 75 minutes.

A) The following was observed when the bacteria originated from a 24-hour dish culture:
In the sensitive strain, a very subtle effect at the high dose (32/16) with some background of extracellular DNA fragments and a subtle cell lysis started to be seen after 20 minutes. This subtle effect was observed 40 minutes after the low dose (8/4), whereas it was somehow greater with the high dose. The effect became maximum with a subtle background of extracellular DNA fragments and the lysis of virtually all cells 60 minutes after the low dose, and an extensive background and lysis after the high dose.
The strain with intermediate sensitivity started to show a clear effect much later than the sensitive strain, 60 minutes and only after the high dose (32/16). This effect was more obvious after 75 minutes.
The resistant strain did not show any effect at all, although 75 minutes after the high dose (32/16), some isolated cells were moderately lysed such as in FIG. 1c".

B) The following was observed when the bacteria originated from a liquid culture in exponential growth phase:
In the sensitive strain, an effect started to be observed after 10 minutes. This was very subtle at the low dose (8/4) and more prominent with the high dose (32/16). The intensity of the effect increased progressively, after 30 minutes the effect being very similar to that observed after 60 minutes in bacteria originated from a dish culture.
The strain with intermediate sensitivity started to show a clear effect much later than the sensitive strain, 30-40 minutes and only after the high dose (32/16). This effect was more obvious after 60 minutes.
The resistant strain did not show any effect at all, although 60 minutes after the high dose (32/16), some isolated cells were moderately lysed such as in FIG. 1c".

In conclusion:
1) The state of growth of the bacteria influences the sensitivity to antibiotic. It is well known that nongrowing cells which are in stationary phase considerably reduce their sensitivity to β-lactam antibiotics.

2) From the practical point of view, in order to safely distinguish sensitive strains of *E. coli* from the others, it is sufficient to incubate them with the antibiotic for 30 minutes if they are in exponential growth phase (fresh liquid culture), or for 40-60 minutes if they originate from a 24-hour dish culture. If the dish is older or the liquid culture has reached the exponential phase, the incubation time of the bacteria sample with the antibiotic in a liquid medium can be prolonged for several hours. When assessing clinical samples, it is recommendable to simultaneously process a sensitive strain, a strain with intermediate sensitivity and a resistant strain as a control of the antibiotic activity and the effectiveness of the technique.

Example 4

Determination of the Sensitivity or Resistance of Different Gram+ and Gram– Germs to Different Beta-Lactam Antibiotics (Penicillins, Cephalosporin and Carbapenem)

Different bacterial strains grown on a dish with Mueller-Hinton medium for 24 hours were subsequently exposed to a β-lactam antibiotic for 60 minutes in Mueller-Hinton liquid medium at 37° C., under stirring, and were finally processed by means of the technique for evaluating cell wall integrity according to the present invention.

The strains and the antibiotics used were:

Gram+
*Enterococcus faecalis*. Ampicillin-sensitive (MIC=4) and benzylpenicillin-resistant (MIC>32) strain.
*Enterococcus faecium*. Ampicillin-(MIC>32) and benzylpenicillin-resistant (MIC>32) strain.
Gram–
*Acinetobacter baumannii*. Imipenem-(MIC>32) and ceftazidime-resistant (MIC>32) strain.
*Acinetobacter baumannii*. Imipenem-sensitive strain (MIC=0.38) and with intermediate sensitivity to ceftazidime (MIC=12).
*Escherichia coli*. Ceftazidime-sensitive strain (MIC=1) with intermediate sensitivity to ampicillin (MIC=16).
*Escherichia coli*. Ampicillin-(MIC>256) and ceftazidime-resistant (MIC=32) strain.

The doses of antibiotic applied were 0, the MIC determined in the Microbiology Laboratory by means of the microdilution and/or E-test technique, and those of the cutoff points of sensitivity and resistance indicated by the Clinical and Laboratory Standards Institute (CLSI) for each strain. A dose 10 times higher than the MIC was also used.

The cutoff points of the antibiotics vary for each strain:

| *Enterococcus.* | Ampicillin (Resistant) | ≤8 | (Sensitive) | ≥16 |
|---|---|---|---|---|
| *Acinetobacter.* | Ceftazidime (Resistant) | ≤8 | (Sensitive) | ≥32 |
| | Imipenem (Resistant) | ≤4 | (Sensitive) | ≥16 |
| *E. coli.* | Ampicillin (Resistant) | ≤8 | (Sensitive) | ≥32 |
| | Ceftazidime (Resistant) | ≤8 | (Sensitive) | ≥32 |

Figure 2:
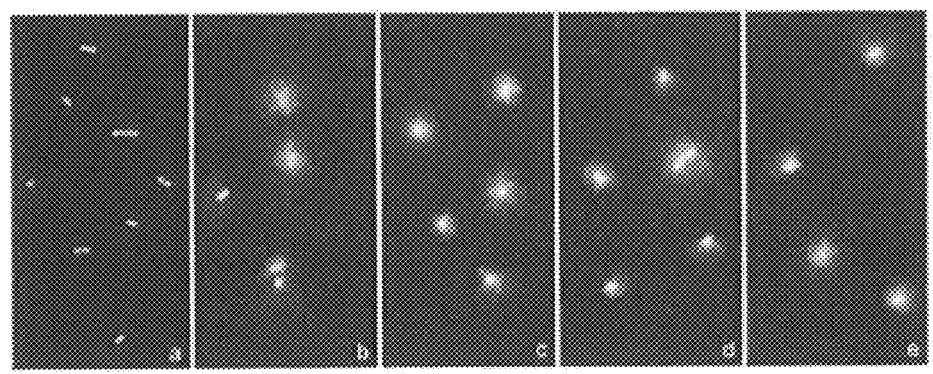
FIG. 2 shows *Enterococcus faecalis*, a Gram+ bacterium that is sensitive to β-lactam antibiotic, ampicillin (MIC=4 µg/mL), treated with different doses of ampicillin for 60 minutes. a: antibiotic-free control; b: 4 µg/mL (MIC); c: 8 µg/mL; d: 16 µg/mL; e: 32 µg/mL. The MIC dose is sufficient to observe the effect on the wall by the antibiotic and the background of extracellular DNA fragments.
Figure 3:
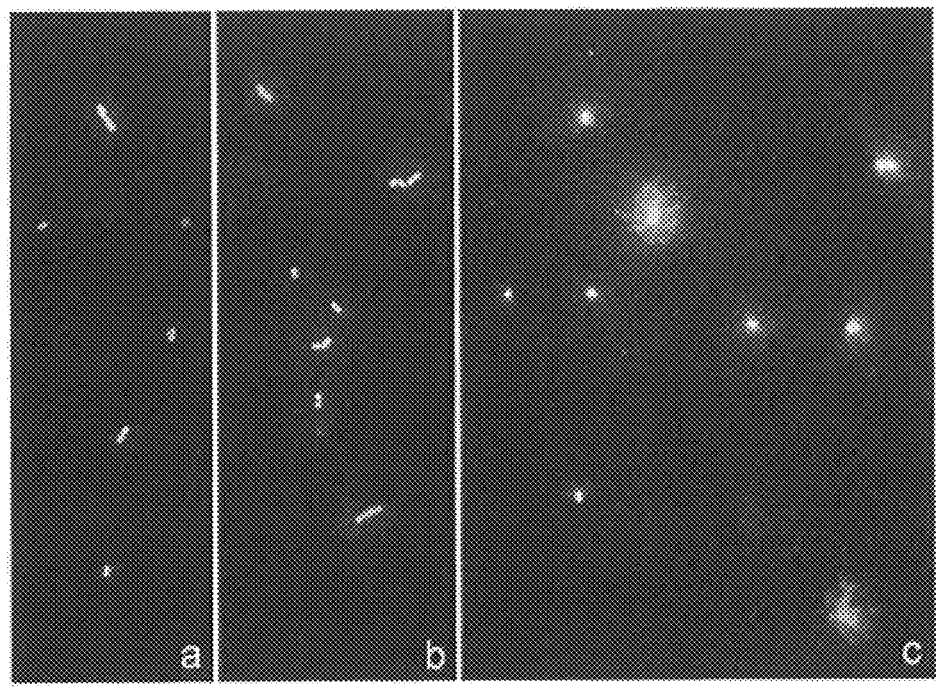
FIG. 3 shows *Enterococcus faecium*, a Gram+ bacterium that is resistant to β-lactam antibiotic, ampicillin (MIC>32), incubated with different doses of this antibiotic for 60 minutes. a: antibiotic-free control; b: 32 µg/mL; c: 320 µg/mL. After 320 µg/mL, an effect on the wall of some isolated cells was observed with a subtle background of extracellular DNA fragments.

Results
Gram+
*Enterococcus faecalis*. Ampicillin-sensitive (MIC=4) and benzylpenicillin-resistant (MIC>32) strain.
Incubation with ampicillin: 0, 4 (MIC), 8, 12, 16, 40 μg/mL. After incubating with a dose of 4 μg/mL (MIC), the effect on the wall was observed in most cells, the cells being lysed in a heterogenous manner with a subtle background containing DNA fragments. Heavily lysed: 35%; moderately lysed: 25%; lysed with fragmented DNA: 12%; non-lysed: 28%. A similar result was observed after incubating with a dose of 8, 12 and 16 μg/mL. After a dose of 40 μg/mL, the background becomes very faint with very little cells, 63% non-lysed, 15% have a small halo indicating an effect on the wall, 20% have a large lysis halo, and 2% are lysed with fragmented DNA nucleoid (FIG. 2).
Incubation with benzylpenicillin: 0, 0.06, 16, 32, 320 μg/mL. After incubating with a dose of 16 μg/mL, some background which somewhat increases after incubating with doses of 32 and 320 μg/mL is observed. After incubating with a dose of 16 μg/mL, there are 4.5% lysed cells with a large halo. 81% of the cells are not lysed. After incubating with a dose of 32 μg/mL: 4% with a large halo and 4% lysed with nucleoid with fragmented DNA. 65% of the cells are not lysed. After incubating with a dose of 320 μg/mL: 72.3% non-lysed and 25% with a small halo. After incubating with a dose of 16, 32 and 320 μg/mL, many empty faint capsules are observed: 0.5-1.5%.
*Enterococcus faecium*. Ampicillin-(MIC>32) and benzylpenicillin-resistant (MIC>32) strain.
Incubation with ampicillin: 0, 8, 12, 16, 32 (MIC), 320 μg/mL. After incubating with a dose of 320 μg/mL, some effect is observed with a subtle background with 7.5% heavily lysed cells, 1% lysed cells with nucleoid with fragmented DNA, 2% cells with a small halo and 89% non-lysed (FIG. 3).
Incubation with benzylpenicillin: 0, 0.06, 16, 32, 320 μg/mL. After incubating with a dose of 320 μg/mL, there is no background but 5% heavily lysed cells are observed. The remaining cells are not lysed.

Gram–
*Acinetobacter baumannii*. Imipenem-(MIC>32) and ceftazidime-resistant (MIC>32) strain. This strain shows a very subtle baseline background.
Incubation with imipenem: 0, 4, 8, 16, 32, 320 μg/mL. After incubating with a dose of 16 μg/mL, there is no background of extracellular DNA fragments, and 1% cells with a large halo, 1% cells with a small halo and 0.5% lysed cells with nucleoid with fragmented DNA are observed. After incubating with a dose of 32 μg/mL, a result similar to that of the incubation with a dose of 16 μg/mL is observed. After incubating with a dose of 320 μg/mL, a subtle background of extracellular DNA fragments is observed, but 92% of the cells are not lysed, 2.5% lysed cells with a small halo, 3.5% heavily lysed cells and 2% lysed cells with nucleoid with fragmented DNA. The non-lysed cells are larger and rounder.
Incubation with ceftazidime: 0, 8, 20, 32, 256, 2.560 μg/mL. After incubating with a dose of 8 μg/mL, 22% of the cells are very elongated and filamentous. At the subsequent doses, 90% of the cells are filamentous. After incubating with a dose of 20 and 32

μg/mL: 84.5% of the cells show a small halo, 1.5% of the cells show a large halo, without background of extracellular DNA fragments. After incubating with a dose of 256 μg/mL: 32.3% of the cells are heavily lysed, 63% of the cells shows a small halo, 4.7% are not lysed, with a subtle background. After incubating with a dose of 2.560 μg/mL, the same background persists, 5% of the cells are not lysed, 6.5% of the cells show a small halo, 63.5% of the cells show a large halo, and 25% are lysed with nucleoids with fragmented DNA.

*Acinetobacter baumannii*. Imipenem-sensitive strain (MIC=0.38) with intermediate sensitivity to ceftazidime (MIC=12). This strain does not have a baseline background.

Incubation with imipenem: 0, 0.038, 0.38 (MIC), 4, 8, 16 μg/mL. After incubating with a dose of 0.038 μg/mL, there is a little background. 75.7% of the cells are not lysed and there is only 1.4% of cells with a large halo and 22.9% of cells with a small halo. After 0.38 μg/mL, there is a clear background. 75.7% of the cells are heavily lysed with a large halo, 5.9% of the cells have a small halo and 7.4% lysed with nucleoid with fragmented DNA. After incubating with a dose of 4, 8 and 16 μg/mL, the background and many faint empty capsules are observed (12% at a dose of 4 μg/mL; 19.5% at a dose of 8 μg/mL; 15% at a dose of 16 μg/mL). There are many lysed cells with nucleoid with fragmented DNA (66% at a dose of 4 μg/mL; 69.5% at a dose of 8 μg/mL; 73.5% at a dose of 16 μg/mL). There are little cells with a large halo (13.5% at a dose of 4 μg/mL; 6% at a dose of 8 μg/mL; 5% at a dose of 16 μg/mL) and some non-lysed cells (8.5% at a dose of 4 μg/mL; 5% at a dose of 8 μg/mL; 6.5% at a dose of 16 μg/mL).

Incubation with ceftazidime: 0, 8, 12 (MIC), 20, 32, 120 μg/mL. After incubating with a dose of 8 μg/mL, there are 82% filamentous cells with a total of 40% of lysed cells with a small halo and 1% of lysed cells with nucleoid with fragmented DNA, without background. After incubating with a dose of 12 μg/mL (MIC) and 20 μg/mL, there are 95% filamentous cells, with 94.5% and 91.5% lysed cells with a small halo, respectively, and 1.5% and 3% lysed cells with a large halo, respectively, and 4% and 5.5% of non-lysed cells, respectively; with a dose of 12 μg/mL, there is a subtle background which increases after a dose of 20 μg/mL. After incubating with a dose of 32 μg/mL, there is more background, 90% elongated cells and 88% lysed cells with a small halo, 6% lysed cells with a large halo and 6% non-lysed cells. After incubating at a dose of 120 μg/mL, an extensive background is observed and there are 91% filamentous cells and 23% lysed cells with a large halo, 67% lysed cells with a small halo, 36% lysed cells with nucleoid with fragmented DNA and 7% non-lysed cells

*Escherichia coli*. Ceftazidime-sensitive strain (MIC=1) with intermediate sensitivity to ampicillin (MIC=16).

Incubation with ampicillin: 0, 8, 16 (MIC), 20, 32, 160 μg/mL. After incubating with a dose of 8 μg/mL, an extensive background is already observed and 55% of the cells are heavily lysed, in addition to 9% lysed with nucleoid with fragmented DNA. After incubating with a dose of 16 μg/mL (MIC): 60.4% lysed cells with a large halo, 5.7% of lysed cells with nucleoid with fragmented DNA, 22.6 empty capsules, 11.3% of non-lysed cells. After incubating with a dose of 20 μg/mL: there are very little cells. 47.3% of the cells show a large halo, 8.6% are lysed cells with nucleoid with fragmented DNA, 31.2% empty capsules, and 12.9% non-lysed cells. After incubating with a dose of 32 and 160 μg/mL, there are very little cells, there being 54% empty capsules.

Figure 4:
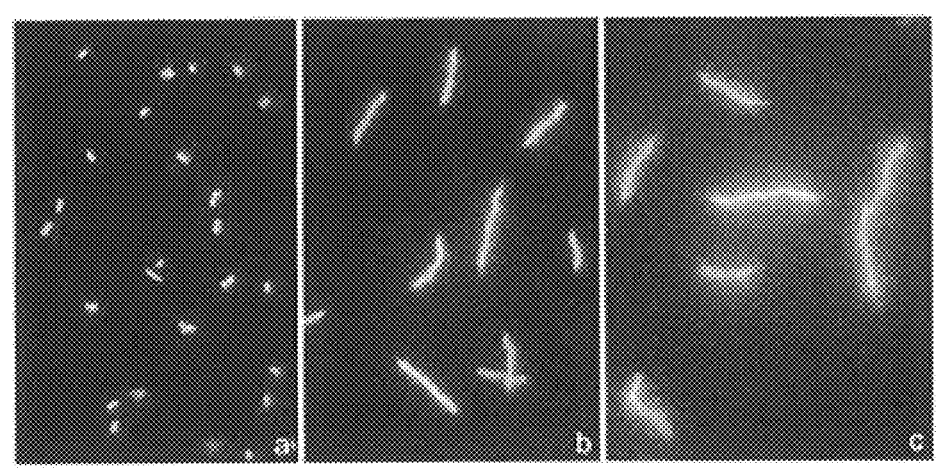
FIG. 4 shows *E. coli* that is sensitive to β-lactam antibiotic, ceftazidime, of the cephalosporin type. The strain was exposed to different doses for 60 minutes. a: antibiotic-free control; b: 1 µg/mL (MIC); c: 8 µg/mL. The MIC gives rise to the filamentous appearance of the cells showing an effect on the wall. After 8 µg/mL, a large effect on the wall is observed, the background of extracellular DNA fragments being clearly seen.

Incubation with ceftazidime: 0, 1 (MIC), 8, 10, 20, 32 μg/mL. After incubating with a dose of 1 μg/mL, there are 99% filamentous cells, 97% heavily lysed with some background (FIG. 4). After incubating with a dose of 8 μg/mL, the result is similar to that obtained when incubating with a dose of 1 μg/mL, but with more background. After incubating with a dose of 10 μg/mL, 76.5% well lysed cells, 11% lysed cells with nucleoid with fragmented DNA and 10.5% empty capsules are obtained with extensive background. After incubating with a dose of 20 and 32 μg/mL, the damage is excessive with 25.3% empty capsules and 20% lysed cells with nucleoid with fragmented DNA, 52.7% well lysed cells and 2% non-lysed cells.

*Escherichia coli*. Ampicillin-(MIC>256) and ceftazidime-resistant (MIC=32) strain.

Incubation with ampicillin: 0, 8, 20, 32, 256, 2560 μg/mL. After incubating with a dose of 256 μg/mL, only 0.5% lysed cells and 1% lysed with nucleoid with fragmented DNA are observed, without background, similar to the baseline and preceding doses. After incubating with a dose of 2,560 μg/mL, the cells are more elongated although not filamentous; 13% of the cells are heavily lysed, 5% moderately lysed, 1.5% lysed with nucleoid with fragmented DNA and 4% empty capsules, with a subtle background.

Incubation with ceftazidime: 0, 8, 20, 32 (MIC), 320 μg/mL. After incubating with a dose of 8 μg/mL, there are 13% filamentous cells, only 1% well lysed cells. After incubating with a dose of 20 μg/mL, there are 99% filamentous cells, 94% non-lysed; 5% well lysed cells and without background. After incubating with a dose of 32 μg/mL, there are 98% filamentous cells, 92% non-lysed cells, 4% well lysed cells, 3% lysed cells with nucleoid with fragmented DNA, 1% empty capsules, with a subtle background. After incubating with a dose of 320 μg/mL, a subtle background is observed with 99% filamentous cells and 95% moderately lysed cells, 3.5% heavily lysed, 0.5% lysed with nucleoid with fragmented DNA, and 1% non-lysed.

Example 5

In Situ Detection of Persisters within Bacterial Population and Their Frequency Quantification The phenomenon of persistence after antibiotic treatments has a great clinical interest. In a bacterial strain population, despite being sensitive to the antibiotic, there may be some cells which tolerate the antibiotic without having any known resistance mechanism, said cells being dormant or slow growing. After removing the antibiotic, some of these cells could grow again and may be responsible for recurrent infection when getting a discontinuous antibiotic treatment. These persisters can be found at a low proportion when the bacteria grow exponentially, but their frequency increases when they enter the stationary phase and during the formation of biofilms (Lewis K. Persister cells, dormancy and infectious disease. Nat Rev Microbiol 2007; 5:48-56).

In the case of β-lactam antibiotics, the persisters are regarded as lacking or having a disabled wall autolysis system which is triggered after the antibiotic treatment. The methodology of the invention could reveal these cells thus providing it with a great value. They could be detected in cultures containing cells sensitive to an antibiotic in a manner much simpler than other methods existing today, such as monitoring cell growth by means of time-lapse microscopy or flow cytometry techniques. These methodologies are complex, laborious, costly, and cannot be used at the clinical level (Roostalu J, Joers A, Luidalepp H, Kaldalu N, Tenson T. Cell division in *Escherichia coli* cultures monitored at single cell resolution. BMC Microbiol 2008; 8:68).

Figure 5:
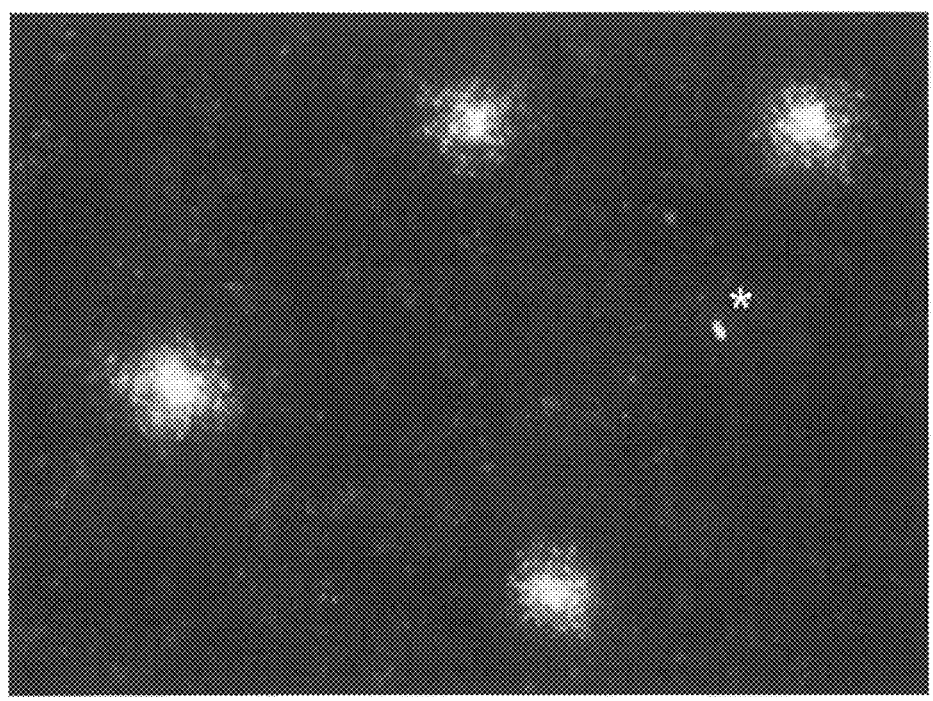
FIG. 5 shows *E. coli* cells originating from a culture in liquid medium, growing in exponential phase, sensitive to amoxicilin/clavulanic acid, and exposed to a high dose of 32/16 for 90 minutes. After processing using the technique of the invention, in addition to the cells showing an effect on the wall that release nucleoid, and to the background of extracellular DNA fragments, a cell with intact morphology (asterisk) that has not been affected by the antibiotic is clearly observed. This cell behaves like a "persister".

FIG. 5 shows cells of a sensitive strain of *E. coli* originating from a culture in a liquid medium, growing in exponential phase, sensitive to amoxicilin/clavulanic acid, and exposed to a high dose (32/16) for 90 minutes. In addition to the cells with affected wall and to the background of extracellular DNA fragments, a cell with intact morphology not at all affected by the antibiotic which must logically correspond to a persister is clearly observed.

Since the persisters cells do not grow, their relative proportion on the slide should increase progressively as the incubation time with the antibiotic increases and the sensitive cells gradually disappear from the culture. This phenomenon could also occur when the strain is incubated with progressively increasing doses of antibiotic for a specific time. In reality, if the results were adjusted to the amount of cells present after the incubation with the antibiotic, cells without halo (persisters) would remain constant regardless of the dose of antibiotic or the incubation time with the antibiotic since they do not grow, whereas the rest of the sensitive cells with halo would decrease progressively as they disappear from the culture. Whether the non-lysed cells correspond to persisters can be determined with these two types of experiments, among others.

A) Incubation with increasing dose of antibiotic. A strain of ampicillin-sensitive *E. coli* is incubated with increasing doses of the antibiotic for 60 minutes. Table 1 shows that the percentage of non-lysed cells increases with the dose of antibiotic, whereas the percentage of lysed cells decreases accordingly. When they are according to relative OD 600, i.e., to the relative number of cells in the culture after each dose, it is seen that the relative proportion of non-lysed cells tends to be between 5-8.5, whereas the relative proportion of lysed cells decreases considerably as the dose increases.

TABLE 1

Results of the incubation of a sensitive strain of *E. coli* with increasing doses of ampicillin for 60 minutes. The % of cells was normalized by means of OD 600.

| DOSES | $OD_{600}$ ($OD_{initial}$ = | RELATIVE | Non-lysed Cells | | Lysed Cells | |
|---|---|---|---|---|---|---|
| µg/mL | 0.1) | $OD_{600}$ % | % | Relative | % | Relative |
| 0 | 0.416 | 100.0 | — | — | 2.3 | 2.3 |
| 2 | 0.323 | 77.6 | 9.7 | 7.5 | 90.3 | 70.1 |
| 8 | 0.120 | 28.8 | 29.3 | 8.5 | 70.6 | 20.4 |
| 16 | 0.050 | 12.0 | 62.5 | 7.5 | 37.5 | 4.5 |
| 32 | 0.027 | 6.5 | 77.5 | 5.0 | 22.5 | 1.5 |
| 160 | 0.024 | 5.8 | 85.0 | 4.9 | 15.0 | 0.9 |

Figure 6:
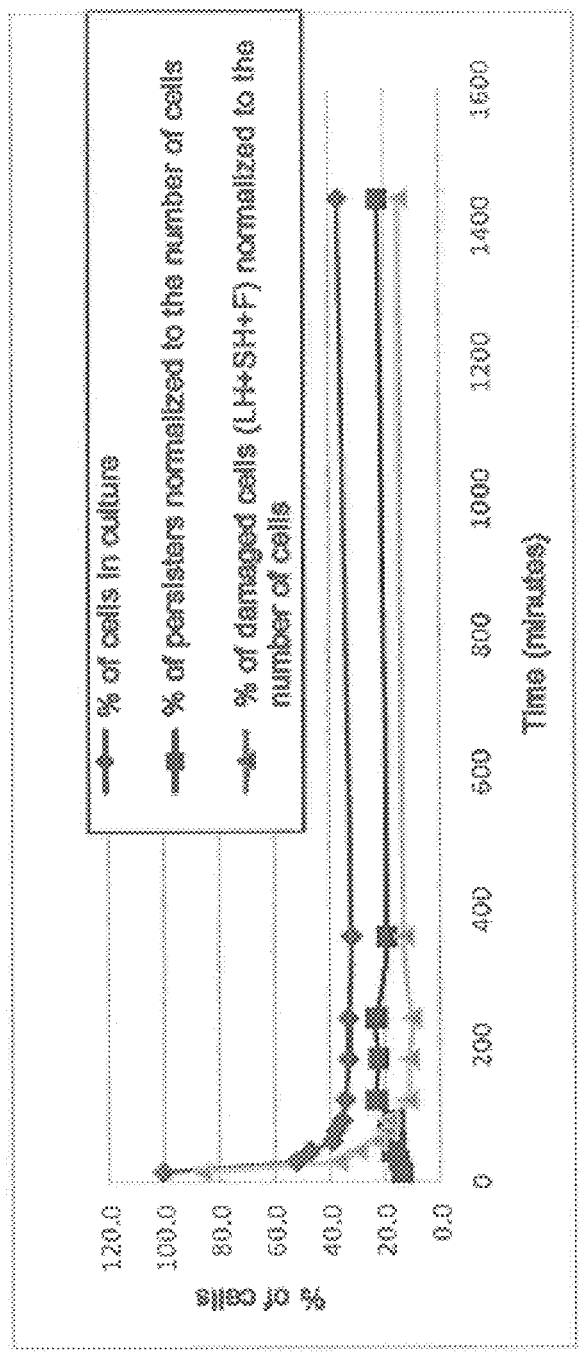
FIG. 6 shows graphs depicting the percentages of cells in culture, of cells without halo and of cells with damaged wall, of *E. coli* originating from a culture in liquid medium, growing in exponential phase, sensitive to amoxicilin/clavulanic acid, and exposed to a high dose of 32/16 for different times. It is observed at the top that the proportion of non-lysed cells increases gradually in the culture over time as the cells affected by the antibiotic gradually decrease (LH: large halo+SH: small halo+F: lysed with fragmented DNA). At the bottom, the same drawing, but the data of which have been normalized according to the percentage of cells remaining in the culture, is shown. It is observed that the percentage of cells without halo tends to remain constant over time, whereas the percentage of cells with damaged wall gradually decreases in the manner similar to that of the cells in culture. This supports that cells without halo behave like "persisters".

B) Incubation with antibiotic for increasing time periods. A strain of amoxicilin/clavulanic acid-sensitive *E. coli* was incubated with a dose of antibiotic of 32/16 for 24 hours. Aliquots to be studied were extracted from the culture for the times specified in FIG. 6. The top portion of FIG. 6 shows that the proportion of non-lysed cells increases gradually in the culture over time, as the cells affected by the antibiotic gradually decrease. In fact, the curve of the drop of the percentage of cells with halo is similar to the drop of the percentage of cells in culture, measured by means of a Neubauer chamber. If the percentage of cells of each type is normalized with respect to the percentage of cells remaining in culture, the level of cells without halo tends to remain constant over time, whereas the level of cells with damaged wall decreases progressively, in the manner similar to cells in culture (FIG. 6, bottom portion).

In conclusion, both types of experiments indicate that cells without halo remain in the culture with antibiotic over time and with different increasing doses of antibiotic. This supports their persister status since they neither grow nor are affected by the antibiotic, their frequency must be independent from the dose of antibiotic and from the incubation time with the antibiotic.

Example 6

Determination of Nucleoids with Fragmented DNA Exclusively in Cells with Cell Wall Affected by the Antibiotic A sensitive strain and another strain with intermediate sensitivity of *E. coli* in exponential growth were exposed to amoxicilin together with clavulanic acid in Mueller-Hinton liquid medium. The dose was 32/16 (amoxicilin/clavulanic acid). The incubation time with the antibiotic was 15 minutes, 30 minutes, 1 hour, 2 hours, 4 hours and 6 hours. Simultaneously, an antibiotic-free control of the strain was also processed at the same time.

The frequency of nucleoids with fragmented DNA was determined according to the protocol described by Tamayo et al. (Tamayo M, Santiso R, Gosálvez J, Bou G, Fernández J L. Rapid assessment of the effect of ciprofloxacin on chromosomal DNA from *Escherichia coli* using an in situ DNA fragmentation assay. BMC Microbiology 2009; 9: 69). This protocol lyses all the cells regardless of the state of their wall. This is a suitable technique for evaluating the state of the nucleoid DNA of all the cells in a population. On the other hand, such nucleoid was also determined in the processed preparations to recognize an effect on the cell wall according to the protocol of the present invention. This method is not suitable because it does not allow estimating the state of the DNA in non-lysed cells, the cell wall of which is not affected by the antibiotic. However, given that in this experiment most of the cells are affected by the antibiotic, this allows estimating DNA fragmentation exclusively in cells with damaged wall. This is important because it allows evaluating the theory indicating that cells having the cell wall affected by the antibiotic would generate a late response that would end up also affecting the nucleoid DNA, which would later be fragmented during the cellular death process, possibly by producing free oxygen radicals (Kohanski, M A, Dwyer D J, Hayete B, Lawrence C A, Collins J J. A common mechanism of cellular death induced by bactericidal antibiotics. Cell 2007; 130:797-810).

Figure 7:
FIG. 7 shows *E. coli* cells originating from a culture in liquid medium, growing in exponential phase, sensitive to amoxicilin/clavulanic acid, and exposed to a high dose of 32/16 for 60 minutes. After processing using the technique of the invention, three cells that release nucleoid were observed in addition to the typical background. One of the nucleoids does not maintain an intact morphology, rather it is shown to be fragmented, stained to a much lesser extent and more diffused (asterisk), showing a wide halo with small DNA fragments that diffused from the central bacterial residual.

FIG. 7 shows several cells processed using the method for determining an effect on the cell wall. One of the nucleoids has fragmented DNA. Unlike the intact nucleoids, the latter is more lightly stained, taking up a larger surface due to the halo of DNA fragment diffusion from the central bacterial area or residual.

Example 7

Determination of Sensitivity or Resistance to a β-Lactam Antibiotic without Using Lysis, Assessing the Background of Extracellular DNA Fragments in the Preparation When the bacteria are processed without the step of incubating in lysis solution, these bacteria are all practically intact, regardless of whether or not they are affected by the antibiotic. However, if after appropriate incubation with the cutoff dose of antibiotic for sensitive strains, a diffused homogeneous microgranular-fibrillar background containing DNA fragments given off by the cells may or may not be seen in the preparation, whether or not the strain is sensitive can be clearly known. This assessment of the background without using lysis to observe the effect on cell wall can be performed by staining the material included in microgel, or the material not included in microgel, either fixed or fresh, with fluorochrome.

In the case of a pure culture, the assessment of the background containing DNA fragments present in the preparation made without using lysis may be sufficient to determine if a strain is sensitive or resistant after the suitable incubation time with bacterial wall-specific antibiotic. This can perhaps speed up the time for obtaining the result even more when time is pressing due to clinical urgency.

A) Material Included in Microgel

Figure 8:
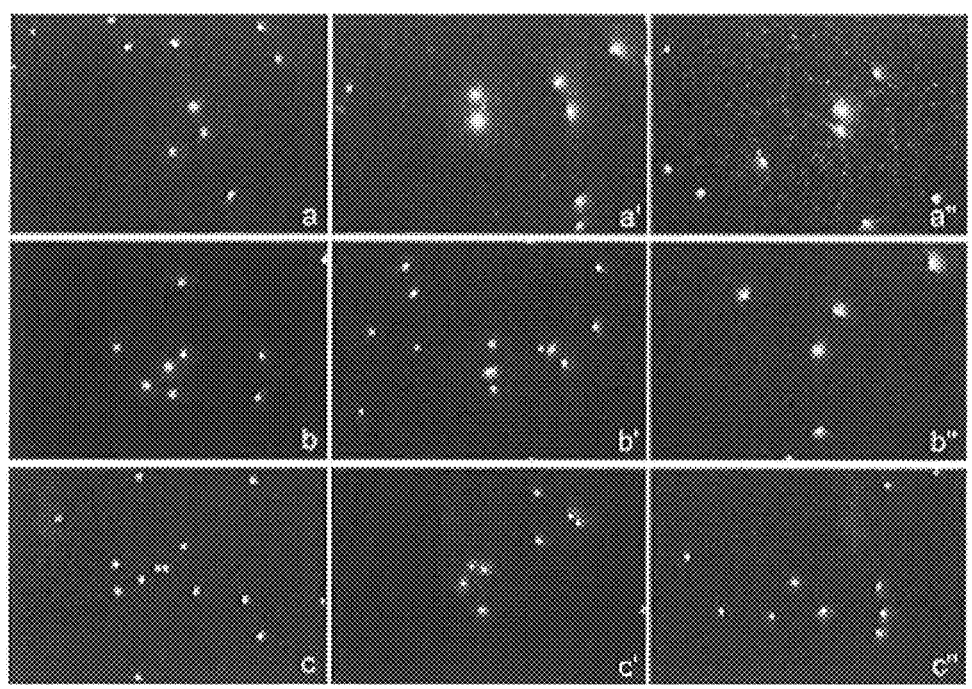
FIG. 8 shows the same strains of *E. coli* presented in FIG. 1 which were cultured for 24 hours on a dish and then for 40 minutes in a liquid medium with a dose of 0 (a, b, c), 8/4 (low dose; a', b', c') and 32/16 (high dose; a", b", c") of amoxicilin/clavulanic acid. The strains were processed without the step of lysis by exposure to the lysis solution. The sensitive strain is shown in the top row (a, a', a"); the strain with intermediate sensitivity in the central row (b, b', b") and the resistant strain in the bottom row (c, c', c"). In those growth conditions and after this incubation period with the antibiotic, only the sensitive strain shows the diffused homogeneous microgranular-fibrillar background of extracellular DNA fragments given off by the cells. This background is evident after the low dose (8/4) and increases significantly after the high dose (32/16). The sensitive strain can thus be clearly differentiated from the others.

The liquid with the cells is included in an agarose microgel which is dehydrated in alcohols and/or air dried or dried in an oven and stained with fluorochrome. It is the same process described in detail above, but without incubation with lysis solution. The background can be evaluated rapidly after 15-20 minutes that it takes to perform the technique. The preparations are permanent. The result is shown in FIG. 8, showing the same strains presented in FIG. 1, grown for 24 hours on a dish and then incubated for 40 minutes with a dose of amoxicilin/clavulanic acid of 0, 8/4 (low) and 32/16 (high). This shortened system does not allow detecting the persisters of the bacterial strain itself, or distinguishing sensitive cells from resistant cells, in the case of a mixed or contaminated culture. Furthermore, the intensity of the background of extracellular DNA fragments depends on the concentration of sensitive bacteria. If there is a small concentration, the background can be very faint or almost unobservable. Therefore, a strain of amoxicilin/clavulanic acid-sensitive E. coli incubated with a high concentration (32/16) shows, starting from an OD 600 of 0.07, a very clear background after 15 minutes of incubation (OD 600: 0.071; 42.5 million of cells per mL, measured by means of a Neubauer chamber; 5.62% viable cells) and the background remains intense up to 2 hours of incubation (OD 600: 0.033; 14.5 million of cells per mL; 3.77% viable cells). The background becomes poor after 3 and 4 hours (OD 600: 0.037 and 0.033 respectively; 14 million of cells per mL at both 3 and 4 hours; 0.38% viable cells at both 3 and 4) and is no longer observed after 6 hours (OD 600: 0.035; 13.5 million of cells per mL; 0.13% viable cells). Even though the total cells are maintained between 40-30% with respect to the initial cells from 60 minutes to 6 hours, the intensity of the background containing DNA fragments gradually decreases during that time until it is no longer detectable, possibly due to degradation thereof.

B) Fixed Material

An aliquot of the antibiotic-free culture and other aliquots with the doses of antibiotic can be mixed with a fixation agent. Alcoholic fixation agents, aldehyde fixation agents or ketone fixation agents such as methanol, ethanol, acetone, formaldehyde, glutaraldehyde, as well as acetic acid, picric acid, mercury chloride, dichromate ion, osmium tetroxide, etc, and mixtures such as methanol:acetic acid at a ratio of 3:1 for example, and Carnoy's fluid, can be used. In the case of formaldehyde, the solution can be a 0.1 to 50%, preferably 10%, aqueous solution. In the case of the other fixation agents, they can be used at different proportions from 0.1 to 100%. A proportion of 5-10% of an aqueous solution containing microorganisms and 95-90% of fixation agent is recommended. The advantage of fixing over wet mount observation is that the material can be stored for a longer time and observed when appropriate. A drop (a few microliters) is spread on the slide and is left to dry. The fluorochrome SYBR Gold (1:400) is then added, a cover slip is laid and the slide is examined. The formaldehyde only preserves the background for a short time period, so it is not recommended. Other fixation agents are more long-lasting and give a clear image of the background.

Figure 9:
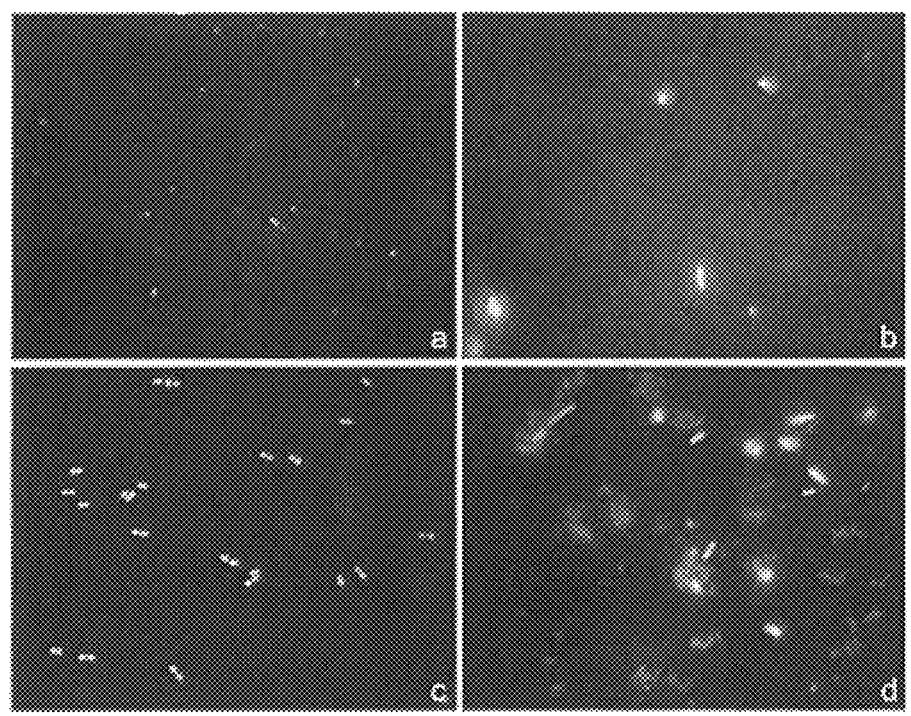
FIG. 9 shows an ampicillin-sensitive strain of E. coli that was incubated with a dose of 8 μg/mL of said antibiotic for 60 minutes. a and b: Wet mount observation. a: antibiotic-free control culture; b: culture treated with ampicillin. A diffused microgranular or fibrillar background of extracellular bacterial DNA fragments is seen among the bacteria in the culture treated with ampicillin. c and d: culture fixed in methanol:acetic acid. c: antibiotic-free control culture; d: culture treated with ampicillin, wherein the background material of DNA is seen among the bacteria, forming aggregates of various shapes and sizes.

The methanol:acetic acid is preferred. With the methanol:acetic acid, the material is more readily spread on the slide, the background material and the bacteria adhere better to the glass, whereas with the other fixation agents they will most likely become detach during staining since it is not previously incubated with dry heat. The background of extracellular DNA fragments is observed as a dispersed aggregate (FIG. 9). The spread of the material fixed on the slide takes 8-10 minutes to dry, although when the slide is placed on a dish or in an oven at 37° C. it dries in 5 minutes. If the methanol:acetic acid (3:1) is 95%, the drying after spreading the drop is quick, in less than 1 minute. Although the materials are simple, the fixings do not provide great advantage in terms of the preparation and observation time, with respect to the microgel preparation, which is also permanent. Therefore, in view of a first rapid provisional sensitivity or resistance determination, the operativity of the fixing or of the use of the microgel is practically similar.

C) Fresh Material

The fluorochrome is added to an aliquot of the culture, a cover slip is placed and the slide is directly examined under the fluorescence microscope. For example, 2 μL of fluorochrome SYBR Gold (1:400) are added to about 10 μL of liquid culture with bacteria. This is performed in cultures with antibiotic acting on the cell wall, including an antibiotic-free control culture. In the culture with the antibiotic, in addition to the floating bacteria, diffused intercellular microfilamentous or granular material in continuous Brownian motion is observed, corresponding to the background emitted by the sensitive bacteria (FIG. 9). This 1-minute determination of the sensitivity or resistance to the antibiotic acting on the cell wall is the fastest and simplest. In any case, it depends on the cell concentration, the capacity of the sensitive cell to release cellular material, the purity of the strain, incubation time with the antibiotic, dose of antibiotic, etc. A lysed bacterium which releases DNA nucleoid can sometimes be observed, but most bacteria do not behave as such. The technique does not allows detecting the persisters of the bacterial strain itself, or distinguishing sensitive cells from resistant cells, in the case of a mixed or contaminated culture. Finally, the image quality is not as clear and sharp as in the case of inclusion in microgel, and the preparation is not permanent, so it cannot be stored and examined in the future unless it is not be frozen.

When the bacteria growing in a liquid medium with a wall-specific antibiotic to which they are sensitive are centrifuged, the bacteria accumulate forming pellet, whereas the extracellular DNA fragments remain in the supernatant fraction. An aliquot of this supernatant fraction can be stained with the fluorochrome to be assessed, in a wet mount observation or fixed or processed in a microgel. Therefore, rapid information concerning the sensitivity or resistance to the antibiotic is also obtained. The assessment of this background of extracellular DNA fragments can be performed not only by means of the microscopy, but also by any other alternative physical or chemical method for detecting DNA (electrophoresis, antibodies, spectrophotometry, polymerase chain reaction, hybridization techniques, microarrays, microfluidics, nanoparticles, quantum dots, etc).

Example 8

Evaluation of the Nature of the Microgranular-Fibrillar Background Observed in the Preparations of Cultures Containing Bacteria Sensitive to Cell Wall-Specific Antibiotics To investigate the nature of the microgranular-fibrillar background observed in the preparations of cultures containing bacteria sensitive to cell wall-specific antibiotics, an in situ digestion with enzymes (proteinase K and DNAase I), an in situ fluorescent hybridization (FISH) and microgel staining of diluted culture were carried out.

A) In Situ Incubation with Proteinase K, an Enzyme that Degrades Proteins, and with DNAase I, an Enzyme that Digests DNA The experiment was conducted with a strain of ampicillin-sensitive E. coli and a strain of imipenem-sensitive A. baumanii. The first strain was incubated with 32 µg/mL ampicillin and the second strain with 0.76 µg/mL imipenem for 60 minutes in Mueller-Hinton liquid medium at 37° C. under stirring. After incubation, each culture with the cells was included in microgels on the slide. A microgel containing the antibiotic-free control culture, and 2 microgels containing the culture treated with antibiotic were placed on each slide. The size of each microgel corresponds to a 18×18 mm slide cover. The microgels on some slides were washed in a proteinase K buffer (1% SDS, 2 mM EDTA) and the microgels on other slides were washed in a DNAase I buffer (20 mM Tris-HCl, pH 8.3, 2 mM $MgCl_2$). In the former, one of the microgels containing the culture treated with ampicillin was incubated only with a proteinase K buffer and the other microgel containing the culture treated with ampicillin was incubated with 5 µl of 2 mg/mL proteinase K, in the buffer thereof. In the slides washed with a DNAase I buffer, one of the microgels containing the culture treated with ampicillin was incubated only with a DNAase I buffer and the other microgel containing the culture treated with ampicillin was incubated with 5 µl of 2.5 U DNAase I, in the buffer thereof. The incubations were carried out for 30 minutes at 37° C. in a humidity chamber. The slides were then washed in distilled water, dehydrated in increasing alcohols, dried and stained with SYBR Gold (1:400).

Figure 10:
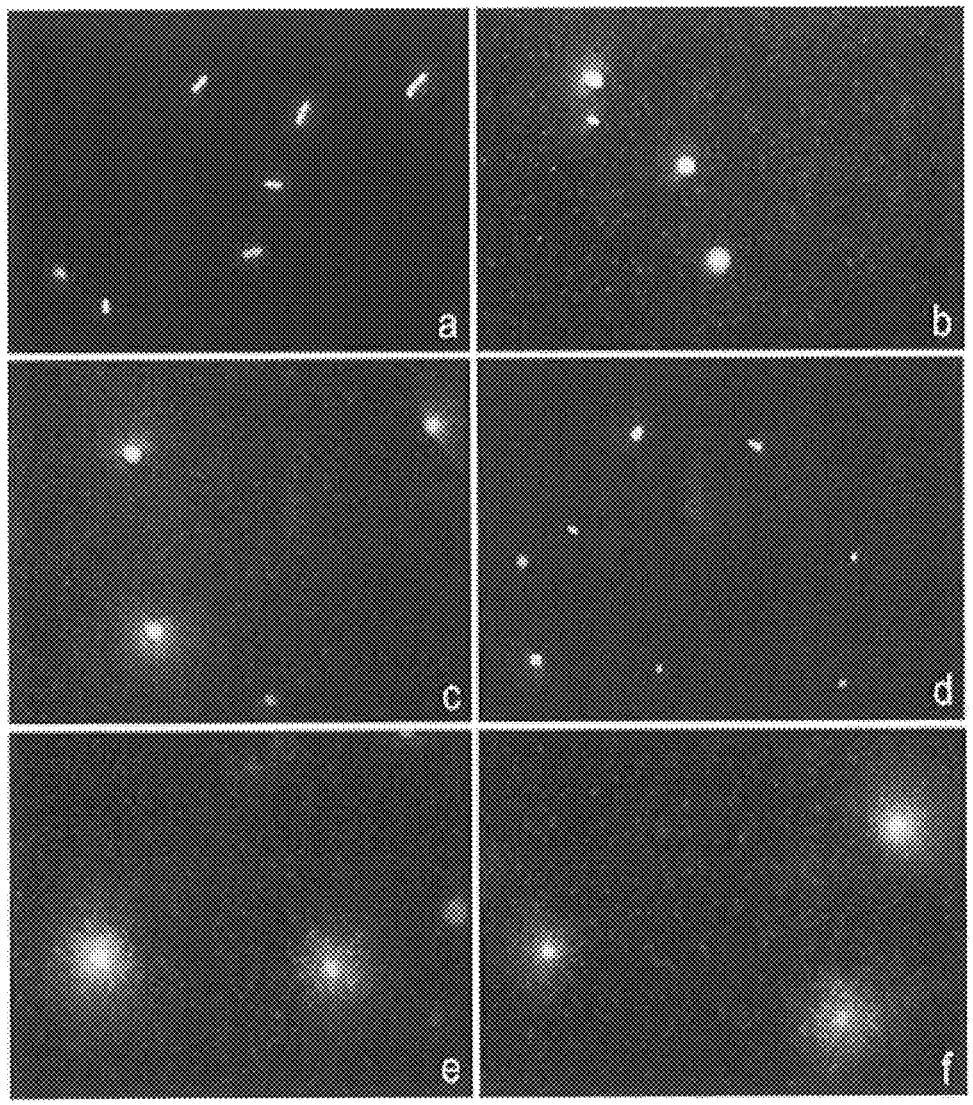
FIG. 10 shows a ampicillin-sensitive strain of E. coli that was incubated with a dose of 32 μg/mL of said antibiotic for 60 minutes. Aliquots of an antibiotic-free control culture and aliquots of the culture with ampicillin treatment were included in microgels and were stained with SYBR Gold. The antibiotic-free control culture does not show microgranular-fibrillar background in the preparation (a), whereas the culture treated with ampicillin shows said background (b). The incubation of the microgels with buffers containing the enzymes, DNAase I (c) or proteinase K (e), does not affect said background. When the microgel of the cultures treated with ampicillin is incubated with 2.5 U DNAase I for 30 minutes, the background disappears from the preparation (d), whereas when it is incubated with 2 mg/mL proteinase K for 30 minutes, the background remains unchanged (f). The buffer containing proteinase K has SDS and EDTA which lyses the cells. Increasing the concentration of proteinase K to 10 mg/mL in the same buffer or in water does not affect the background either. This experiment demonstrates that the background corresponds to extracellular DNA fragments.

Result:

The cultures that are not treated with ampicillin or imipenem did not show microgranular-fibrillar background in the preparation (FIG. 10a). The cultures treated with ampicillin or imipenem showed the background which was maintained in the microgels incubated exclusively with the buffers of the enzymes (FIGS. 10b, 10c and 10e). When it was incubated with proteinase K, the background remained unchanged (FIG. 10f), whereas when it was incubated with DNAase I, the background disappeared (FIG. 10d). Increasing the concentration of proteinase K to 10 mg/mL in the same buffer or in water does not result in a effect on the background either, whether in a microgel or in a spread in Carnoy. This indicates that the background observed mainly includes extracellular DNA fragments originating from cells affected by the antibiotic. This background is not observed when using other types of antibiotics, such as quinolones.

B) In Situ Fluorescent Hybridization (FISH) with Whole Genomic DNA Probe of E. coli An ampicillin-sensitive E. coli culture was incubated with 32 µg/mL of said antibiotic for 60 minutes in Mueller-Hinton liquid medium at 37° C. under stirring. 50 µL of the culture were mixed 950 µL with methanol:acetic acid (3:1) and spread on slides. After air drying, the slides were submersed 5 minutes in methanol:acetic acid (3:1) (Carnoy fluid) and left to dry. They were then incubated in 70%, 90% and 100% alcohols at −20° C. for 5 minutes each and left to dry. The DNA present in the slides was denatured by incubating them in 75% formamide/2×SSC, pH 7, at 67° C. for 90 seconds. They were then again passed through 70%, 90% and 100% alcohols at −20° C. for 5 minutes each and left to dry. In each of them, at the level of the spread area, microliters of whole genomic DNA probe of E. coli labeled with biotin were pipetted (4.3 ng/µl in 50% formamide, 2×SSC, 10% dextran sulfate, 100 mM sodium phosphate, pH 7), putting a 18×18 mm cover slip. The probe was incubated overnight in a humidity chamber. The non-hybridized probe was washed in 50% formamide/2×SSC, pH 7, two 5-minute washes and then in 2×SSC, pH 7, two washes 3 minutes each, at 37° C. To reveal the hybridized probe, the slides were incubated in an antibody blocking solution (5% BSA, 4×SSC, 0.1% Triton X-100) for 5 minutes at 37° C. and then in streptavidin-Cy3 (1:200, in 1% BSA, 4×SSC, 0.1% Triton X-100) for 30 minutes. The slides were stained with DAPI (1 µg/mL in Vectashield) and examined under fluorescence microscope.

Figure 11:
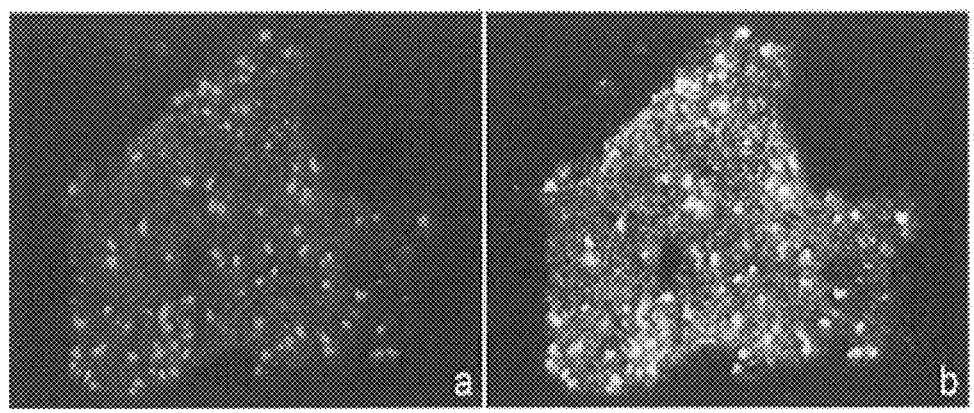
FIG. 11 shows fluorescent in situ hybridization (FISH) with whole genomic DNA probe of E. coli, over extensions of culture, fixed in Carnoy, of said bacterium treated with ampicillin for 60 minutes. Carnoy causes the microgranular-fibrillar material of the background to aggregate, enveloping the bacteria. Therefore, counterstaining with DAPI shows aggregates of the background material with bacteria the nucleoids of which are intensely stained with DAPI. The aggregated background material is also stained with said dye, although more lightly (a). The whole genomic DNA probe hybridizes both with the cell nucleoids and with the background material, demonstrating that the latter corresponds to fragmented bacterial DNA.

Result:

The counterstaining with DAPI shows that in the preparations fixed in Carnoy, aggregates which can surround bacterial cells the nucleoids of which are stained with DAPI are seen in the background. The dye of the DNA readily penetrates due to the absence of wall in said cells. The DAPI also stains the aggregated background but more lightly (FIG. 11a). By examining the hybridization signal of the probe, it is observed that the nucleoids of the cells, lacking wall due to the antibiotic treatment, hybridize with the whole genomic DNA probe. The aggregated background shows intense hybridization signal (FIG. 11b), demonstrating in a conclusive manner that it corresponds to bacterial DNA.

Figure 12:
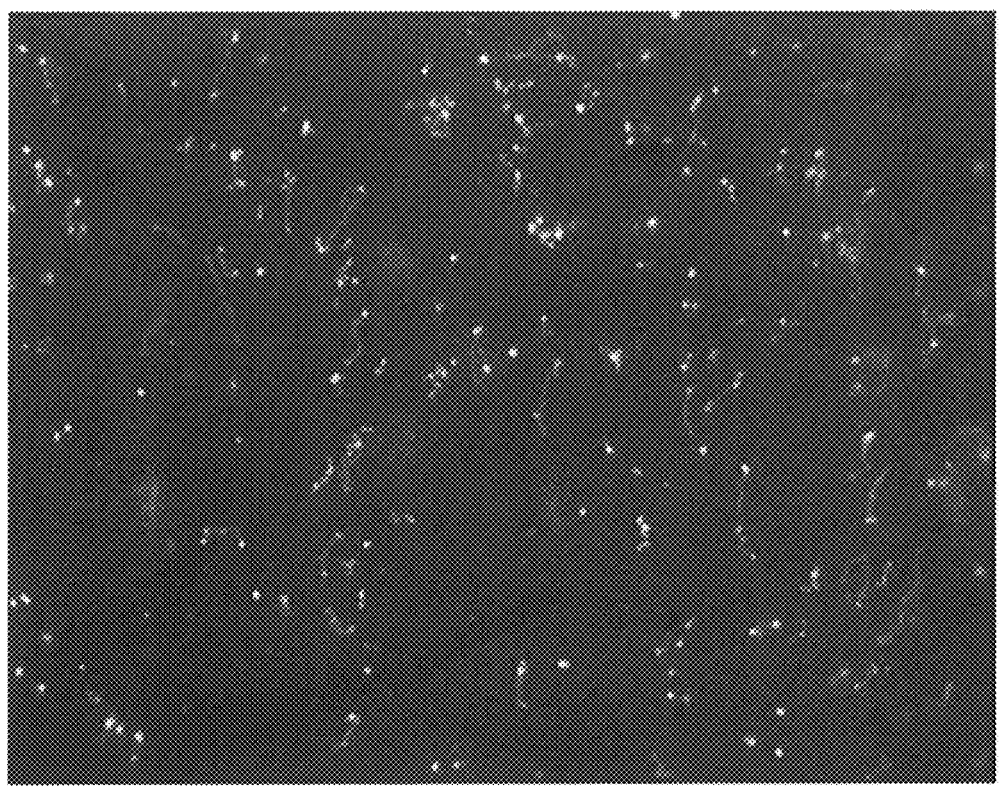
FIG. 12 shows an imipenem-sensitive strain of Acinetobacter baumannii that was incubated with 0.76 μg/mL of this antibiotic for 1 hour. An aliquot of the culture was diluted and included in an agarose microgel, dehydrated in increasing alcohols, dried and stained with SYBR Gold. A microgranular-fibrillar background corresponding to DNA fragments in different degrees of lengthening is seen.

C) Staining of Microgel Containing Diluted Culture of Imipenem-Sensitive Acinetobacter baumannii An imipenem-sensitive A. baumannii culture was incubated with 0.76 µg/mL of said antibiotic for 60 minutes in Mueller-Hinton liquid medium at 37° C. under stirring. An aliquot of said culture was diluted 10 times and was included in a microgel without using lysis, it was dehydrated in increasing alcohols, dried and stained with SYBR Gold. The dilution allowed observing in greater detail the appearance of the microgranular-fibrillar background, which corresponds to DNA fragments in different levels of lengthening, from the withdrawn momentary appearance to the extended fibrillar appearance (FIG. 12).

Result:

The microgranular-fibrillar background observed in the microorganism culture medium where the cell wall-specific antibiotic has been effective corresponds to extracellular DNA fragments released by the microorganism.

CONCLUSIONS

As a whole, the results obtained in Examples 1 to 8 clearly show the efficacy of the methods provided by the present invention for the rapid in situ determination of bacterial sensitivity or resistance to antibiotics acting on the cell wall, for example, by inhibiting peptidoglycan biosynthesis. Said results have been verified in tests conducted using different microorganisms (e.g., *Acinetobacter baumanii, Enterobacter cloacae, Escherichia coli, Klebsiella oxytoca, Klebsiella* spp., *Morganella morganii, Proteus mirabilis, Salmonella* spp., *Enterococcus faecalis, Enterococcus faecium, Enterococcus* spp., and *Staphylococcus aureus*) originating from clinical isolates collected in the hospital of A Coruña (Spain) from different patients and antibiotics inhibiting peptidoglycan synthesis (e.g., ampicillin, ceftazidime, imipenem, penicillin and vancomycin) as mentioned by Santiso et al. (Santiso et al., BMC Microbiology 2011, 11:191), the content of which is incorporated by reference.

The technique for evaluating the cell wall integrity provided by this invention is a rapid and simple method which allows distinguishing strains resistant and sensitive to antibiotics acting on the cell wall, for example, by interfering in peptidoglycan biosynthesis. This methodology can be useful not only at the clinical level but also for conducting basic studies on the mechanism of action of antibiotics acting on of the cell wall.

The invention claimed is:

1. A method for evaluating sensitivity of a bacterium to an antibiotic acting on the bacterial cell wall which comprises:
    i) obtaining a pure culture of the bacterium;
    ii) adding to said pure culture of said bacterium an antibiotic;
    iii) adding a lysis solution to the culture resulting from step ii), the lysis solution comprising 200 mM 2-amino-2-hydroxymethyl-propane-1,3-diol, a pH of 10, 0.05-3 M of NaCl, and either 0.025% sodium dodecylsulfate or 5% 4-(1,1,3,3-Tetramethylbutyl)phenyl-polyethylene glycol; and
    iv) determining the presence of bacterial nucleoid in the culture medium, wherein the presence of bacterial nucleoid in the culture medium is indicative that the bacterium is sensitive to the antibiotic.

2. The method according to claim 1, wherein the presence of the bacterial nucleoid in the culture medium is carried out by means of staining.

3. The method according to claim 2, wherein the staining is carried out by means of using one or more fluorochromes.

4. The method according to claim 1, wherein the antibiotic is selected from the group consisting of a β-lactam antibiotic, an isoniazid, an ethionamide, an ethambutol, a cycloserine and a glycopeptide antibiotic.

5. The method according to claim 1, wherein the method comprises step v, before or after step (iii), of immobilizing a sample from the culture on a slide.

* * * * *